(12) United States Patent
Heywood et al.

(10) Patent No.: US 9,589,104 B2
(45) Date of Patent: Mar. 7, 2017

(54) SELF-IMPROVING METHOD OF USING ONLINE COMMUNITIES TO PREDICT HEALTH-RELATED OUTCOMES

(75) Inventors: James Heywood, Newton, MA (US); Benjamin Heywood, Cambridge, MA (US)

(73) Assignee: PATIENTSLIKEME, INC., Cambridge, MA (US)

( * ) Notice: Subject to any disclaimer, the term of this patent is extended or adjusted under 35 U.S.C. 154(b) by 1227 days.

(21) Appl. No.: 12/251,189

(22) Filed: Oct. 14, 2008

(65) Prior Publication Data

US 2009/0131758 A1 May 21, 2009

Related U.S. Application Data

(63) Continuation of application No. PCT/US2008/079674, filed on Oct. 12, 2008.
(Continued)

(51) Int. Cl.
*A61B 5/00* (2006.01)
*G06F 19/00* (2011.01)
(Continued)

(52) U.S. Cl.
CPC .......... *G06F 19/322* (2013.01); *A61B 5/0002* (2013.01); *A61B 5/4824* (2013.01);
(Continued)

(58) Field of Classification Search
USPC ................................................ 600/300–301
See application file for complete search history.

(56) References Cited

U.S. PATENT DOCUMENTS 3,934,226 A 1/1976 Stone et al.
4,712,562 A 12/1987 Ohayon et al.
(Continued)

FOREIGN PATENT DOCUMENTS

DE 370304 C 3/1923
EP 0 912 957 A1 12/2004
(Continued)

OTHER PUBLICATIONS

"Pediatric Research Program Issue APS-SPR" San Diego Convention Center, San Diego, CA May 7-11, 1995. vol. 37, No. 4 Part 2 pp. 139A (Apr. 1995).
(Continued)

*Primary Examiner* — William Thomson
*Assistant Examiner* — Marie Archer
(74) *Attorney, Agent, or Firm* — Locke Lord LLP; Christopher J. Capelli

(57) ABSTRACT

The invention is directed, in part, to method of using self-reported health data in online communities to predict significant health events in life-changing illnesses to improve the lives of individuals and to improve patient self-management. The invention provides a method for providing real-time personalized medical predictions for an individual patient. The method includes: providing a database containing patient information for a plurality of other patients including one or more attributes for each patient in the database; constructing a model of a disease based on disease progressions for the plurality of patients; receiving a request from the individual patient, the patient associated with one or more attributes; and making a real-time prediction for the individual patient based on the mode and the individual patient's attributes.

21 Claims, 8 Drawing Sheets

Related U.S. Application Data

(60) Provisional application No. 60/998,768, filed on Oct. 12, 2007, provisional application No. 61/070,067, filed on Mar. 20, 2008, provisional application No. 60/998,669, filed on Oct. 12, 2007.

(51) Int. Cl.
*G06Q 50/00* (2012.01)
*G06Q 50/22* (2012.01)
*G06Q 50/24* (2012.01)

(52) U.S. Cl.
CPC .......... *A61B 5/4833* (2013.01); *G06F 19/325* (2013.01); *G06F 19/345* (2013.01); *G06F 19/3406* (2013.01); *G06F 19/3437* (2013.01); *G06F 19/3443* (2013.01); *G06F 19/3487* (2013.01); *G06Q 50/22* (2013.01); *G06Q 50/24* (2013.01); *G06F 19/3456* (2013.01); *G06F 19/3481* (2013.01)

(56) References Cited

U.S. PATENT DOCUMENTS

| | | | |
|---|---|---|---|
| 4,899,839 A | | 2/1990 | Dessertine et al. |
| 5,014,798 A | | 5/1991 | Glynn |
| 5,025,374 A | | 6/1991 | Roizen et al. |
| 5,549,117 A | | 8/1996 | Tacklind et al. |
| 5,594,637 A | | 1/1997 | Eisenberg et al. |
| 5,626,144 A | | 5/1997 | Tacklind et al. |
| 5,653,739 A | | 8/1997 | Maurer et al. |
| 5,692,215 A | | 11/1997 | Kutzik et al. |
| 5,692,500 A | | 12/1997 | Gaston-Johansson |
| 5,704,366 A | | 1/1998 | Tacklind et al. |
| 5,713,350 A | | 2/1998 | Yokota et al. |
| 5,720,502 A | | 2/1998 | Cain |
| 5,732,709 A | | 3/1998 | Tacklind et al. |
| 5,812,983 A | | 9/1998 | Kumagai |
| 5,838,313 A | | 11/1998 | Hou et al. |
| 5,937,387 A | | 8/1999 | Summerell et al. |
| 5,950,168 A | | 9/1999 | Simborg et al. |
| 5,984,368 A | | 11/1999 | Cain |
| 5,991,729 A | | 11/1999 | Barry et al. |
| 6,024,699 A | | 2/2000 | Surwit et al. |
| 6,032,119 A | | 2/2000 | Brown et al. |
| 6,081,786 A | * | 6/2000 | Barry et al. ............... 705/3 |
| 6,102,874 A | | 8/2000 | Stone et al. |
| 6,108,635 A | | 8/2000 | Herren et al. |
| 6,108,685 A | | 8/2000 | Kutzik et al. |
| 6,113,552 A | | 9/2000 | Shimazu et al. |
| 6,168,569 B1 | | 1/2001 | McEwen et al. |
| 6,186,145 B1 | | 2/2001 | Brown |
| 6,231,560 B1 | | 5/2001 | Bui et al. |
| 6,234,964 B1 | | 5/2001 | Iliff |
| 6,235,964 B1 | | 5/2001 | Kadash et al. |
| 6,236,983 B1 | | 5/2001 | Hofmann et al. |
| 6,246,992 B1 | | 6/2001 | Brown |
| 6,277,072 B1 | | 8/2001 | Bardy |
| 6,282,441 B1 | | 8/2001 | Raymond et al. |
| 6,283,923 B1 | | 9/2001 | Finkelstein et al. |
| 6,294,999 B1 | | 9/2001 | Yarin et al. |
| 6,314,405 B1 | | 11/2001 | Richardson |
| 6,322,504 B1 | | 11/2001 | Kirshner |
| 6,332,504 B1 | | 12/2001 | Adds et al. |
| 6,334,192 B1 | | 12/2001 | Karpf |
| 6,335,907 B1 | | 1/2002 | Momich et al. |
| 6,339,410 B1 | | 1/2002 | Milner et al. |
| 6,380,858 B1 | | 4/2002 | Yarin et al. |
| 6,400,996 B1 | | 6/2002 | Hoffberg et al. |
| 6,405,034 B1 | | 6/2002 | Tijerino |
| 6,484,144 B2 | | 11/2002 | Martin et al. |
| 6,529,195 B1 | | 3/2003 | Eberlein et al. |
| 6,560,541 B1 | | 5/2003 | Singh |
| 6,587,829 B1 | | 7/2003 | Camarda et al. |
| 6,589,169 B1 | | 7/2003 | Surwit et al. |
| 6,611,846 B1 | | 8/2003 | Stoodley et al. |
| 6,612,985 B2 | | 9/2003 | Eiffert et al. |
| 6,690,397 B1 | | 2/2004 | Daignault, Jr. |
| 6,723,045 B2 | | 4/2004 | Cosentino et al. |
| 6,770,029 B2 | | 8/2004 | Iliff |
| 6,789,091 B2 | | 9/2004 | Gogolak |
| 6,802,810 B2 | | 10/2004 | Ciarniello et al. |
| 6,856,315 B2 | | 2/2005 | Eberlein et al. |
| 6,929,607 B2 | | 8/2005 | Lipman |
| 6,956,572 B2 | | 10/2005 | Zaleski |
| 6,970,742 B2 | | 11/2005 | Mann et al. |
| 6,980,958 B1 | | 12/2005 | Surwit et al. |
| 6,988,075 B1 | | 1/2006 | Hacker |
| 6,999,890 B2 | | 2/2006 | Kai et al. |
| 7,029,441 B2 | | 4/2006 | Dodds |
| 7,039,878 B2 | | 5/2006 | Auer et al. |
| 7,054,758 B2 | | 5/2006 | Gill-Garrison et al. |
| 7,066,883 B2 | | 6/2006 | Schmidt et al. |
| 7,107,547 B2 | | 9/2006 | Cule et al. |
| 7,137,951 B2 | | 11/2006 | Pilarski et al. |
| 7,165,221 B2 | | 1/2007 | Monteleone et al. |
| 7,169,085 B1 | | 1/2007 | Killin et al. |
| 7,251,609 B1 | | 7/2007 | McAlindon et al. |
| 7,286,997 B2 | | 10/2007 | Spector et al. |
| 7,287,031 B1 | | 10/2007 | Karpf et al. |
| 7,302,398 B2 | | 11/2007 | Ban et al. |
| 7,330,818 B1 | | 2/2008 | Ladocsi et al. |
| 7,428,494 B2 | | 9/2008 | Hasan et al. |
| 7,725,328 B1 | * | 5/2010 | Sumner, II ............ G06Q 50/22 600/300 |
| 2001/0034639 A1 | | 10/2001 | Jacoby et al. |
| 2002/0010595 A1 | | 1/2002 | Kapp |
| 2002/0026103 A1 | * | 2/2002 | Norris et al. ............ 600/300 |
| 2002/0072933 A1 | | 6/2002 | Vonk et al. |
| 2003/0065535 A1 | * | 4/2003 | Karlov et al. ............ 705/2 |
| 2003/0125609 A1 | | 7/2003 | Becker |
| 2003/0135128 A1 | | 7/2003 | Suffin et al. |
| 2003/0140063 A1 | * | 7/2003 | Pizzorno et al. ......... 707/104.1 |
| 2003/0187683 A1 | | 10/2003 | Kirchhoff et al. |
| 2003/0233197 A1 | * | 12/2003 | Padilla et al. ............ 702/20 |
| 2004/0015337 A1 | | 1/2004 | Thomas et al. |
| 2004/0103001 A1 | * | 5/2004 | Mazar et al. ............ 705/2 |
| 2004/0122707 A1 | | 6/2004 | Sabol et al. |
| 2004/0132633 A1 | * | 7/2004 | Carter et al. ............ 514/1 |
| 2004/0193448 A1 | * | 9/2004 | Woodbridge et al. ........... 705/2 |
| 2004/0210458 A1 | | 10/2004 | Evans et al. |
| 2004/0267570 A1 | * | 12/2004 | Becker ............ 705/2 |
| 2005/0080462 A1 | | 4/2005 | Jenkins et al. |
| 2005/0085866 A1 | | 4/2005 | Tehrani |
| 2005/0102160 A1 | | 5/2005 | Brown |
| 2005/0108051 A1 | | 5/2005 | Weinstein |
| 2005/0119534 A1 | * | 6/2005 | Trost ............ G06F 19/3431 600/300 |
| 2005/0144042 A1 | | 6/2005 | Joffe et al. |
| 2005/0191716 A1 | | 9/2005 | Surwit et al. |
| 2005/0197545 A1 | | 9/2005 | Hoggle |
| 2005/0197553 A1 | | 9/2005 | Cooper |
| 2005/0272640 A1 | | 12/2005 | Doyle et al. |
| 2005/0283384 A1 | | 12/2005 | Hunkeler et al. |
| 2005/0283385 A1 | | 12/2005 | Hunkeler et al. |
| 2006/0009810 A1 | | 1/2006 | Mann et al. |
| 2006/0010098 A1 | | 1/2006 | Goodnow et al. |
| 2006/0015369 A1 | | 1/2006 | Bachus et al. |
| 2006/0020175 A1 | | 1/2006 | Berry et al. |
| 2006/0030890 A1 | | 2/2006 | Cosentino et al. |
| 2006/0031101 A1 | | 2/2006 | Ross |
| 2006/0036134 A1 | | 2/2006 | Tarassenko et al. |
| 2006/0036294 A1 | | 2/2006 | Tehrani |
| 2006/0036619 A1 | | 2/2006 | Fuerst et al. |
| 2006/0052945 A1 | | 3/2006 | Rabinowitz et al. |
| 2006/0064030 A1 | | 3/2006 | Cosentino et al. |
| 2006/0085217 A1 | | 4/2006 | Grace |
| 2006/0089540 A1 | | 4/2006 | Meissner |
| 2007/0015974 A1 | | 1/2007 | Higgins et al. |
| 2007/0021979 A1 | | 1/2007 | Cosentino et al. |
| 2007/0021984 A1 | | 1/2007 | Brown |
| 2007/0048691 A1 | | 3/2007 | Brown |
| 2007/0060803 A1 | | 3/2007 | Liljeryd et al. |
| 2007/0061166 A1 | | 3/2007 | Ramasubramanian et al. |

(56) References Cited

U.S. PATENT DOCUMENTS

| | | | |
|---|---|---|---|
| 2007/0203423 A1* | 8/2007 | Bardy | 600/529 |
| 2007/0214015 A1* | 9/2007 | Christian | 705/3 |
| 2007/0244372 A1* | 10/2007 | Merkle | 600/300 |
| 2008/0015891 A1* | 1/2008 | Lee | 705/2 |
| 2008/0059232 A1* | 3/2008 | Iliff | 705/2 |
| 2008/0076976 A1* | 3/2008 | Sakurai | G06Q 50/22 600/300 |
| 2008/0140449 A1* | 6/2008 | Hayes | 705/2 |
| 2008/0147440 A1* | 6/2008 | Kil | 705/2 |
| 2008/0147441 A1* | 6/2008 | Kil | 705/2 |
| 2008/0147688 A1* | 6/2008 | Beekmann et al. | 707/100 |
| 2008/0201174 A1 | 8/2008 | Ramasubramanian et al. | |
| 2009/0150180 A1* | 6/2009 | Cohen | G06F 19/3481 705/3 |
| 2010/0286490 A1* | 11/2010 | Koverzin | 600/301 |

FOREIGN PATENT DOCUMENTS

| | | |
|---|---|---|
| EP | 08838326.0 | 12/2013 |
| WO | 00/29983 | 5/2000 |
| WO | 01/50950 | 7/2001 |

OTHER PUBLICATIONS

H. Litt et al., "Graphical Representation of Medical Information in the Visual Chart," Seventh Annual IEEE Symposium on Computer-Based Medical Systems 252-57 (1994).

Deneault, L.G., et al., "An Integrative Display for Patient Monitoring" Conf. Proc. IEEE International Conference on Systems, Man & Cybernetics 515-17 (1990).

Dayhoff, Ruth E. et al., "Providing a Complete Online Multimedia Patient Record" AMIA, Inc. pp. 241-245 (1999).

Long, W., et al. "Web Interface for the Heart Disease Prgoram" AMIA, INc. pp. 762-766 (1996).

Orimo A., et al, "Graphical Output of Health Testing Data," 15(2) Medical Informatics 141-49 (1990).

Merit Cudkowicz et al., "Measures & Markers in Amyotrophic Lateral Sclerosis", 1 NeuroRx 273-83 (Apr. 2004).

Jeana H. Frost & Michael P. Massagli, "Social Uses of Personal Health Information Withing PatientsLikeMe, an Online Patient Community: What Can Happen When Patients Have Access to One Another's Data", 10(3) J. Med. Internet Res. e15 (May 27, 2008).

Leonard E. Baum et al., "A Maximization Technique Occuring in the Statistical Analysis of Probabilistic Functions of Markov Chains", 41(1) Annals of Mathematical Statistics 164-71 (1970).

Donald W. Marquardt, "An Algorithm for Least-Squares Estimation of Nonlinear Parameters" 11(2) J. Soc. Indust. Appl. Math. 431-41 (Jun. 1963).

Jesse M. Cedarbaum et al., "The ALSFRS-R: a revised ALS funcional rating scale that incorporates assessments of respiratory function", 169 J. Neurological Sciences 13-21 (1999).

Francesco Fornai et al., "Lithium delays progression of amyotrophic lateral sclerosis", 105(6) PNAS 2052-57 (Feb. 12, 2008).

J.M. Cedarbaum et al., "Performance of the Amyotrophic Lateral Sclerosis Functional Rating Scale (ALSFRS) in multicenter clinical trials", 152 (Supp. 1) J. Neurol. Sci. S1-S9 (Oct. 1997).

P.H. Gordon et al., Progression rate of ALSFRS-R at time of diagnosis predicts survival time in ALS, 67 Neurology 1314-15 (Oct. 2006).

E.J. Kasarskis et al., Rating the severity of ALS by caregivers over the phone using the ALSFRS-R, 6(1) Amyotrophic Lateral Sclerosis 50-54 (Mar. 2005).

Paul H. Gordon, "Advances in Clinical Trials for Amyotrophic Lateral Sclerosis," 5 Current Neurology & Neuroscience Reports 48-54 (2005).

J. Montes, et al., Development & Evaluation of a self-administered version of the ALSFRS-R, 67 Neurology 1294-96 (Oct. 2006).

International Search Report for International Application No. PCT/US08/79674 (Dec. 16, 2008).

Written Opinion of the International Searching Authority for the International Applicaton No. PCT/US08/79674 (Dec. 16, 2008).

* cited by examiner

ALS FRS Questions
Mapped to Spine Region

| Spinal Region | Speech | Salivation | Swallowing | Handwriting | Food | Dressing | Turning | Walking | Stairs | Syspena | Orthopena | Respiratory |
|---|---|---|---|---|---|---|---|---|---|---|---|---|
| C1 | | | | | | | | | | | | |
| C2 | • | | • | | | | | | | | | |
| C3 | • | • | • | | | | | | | • | • | • |
| C4 | | • | • | | | | | | | • | • | • |
| C5 | | | | | • | • | • | | | • | • | • |
| C6 | | | | • | • | • | • | | | | | |
| C7 | | | | • | • | • | • | | | | | |
| C8 | | | | • | • | • | | | | | | |
| T1 | | | | • | • | • | | | | • | • | |
| T2 | | | | | | • | | | | • | • | |
| T3 | | | | | | • | | | | • | • | |
| T4 | | | | | | • | | | | • | • | |
| T5 | | | | | | • | | | | • | • | |
| T6 | | | | | | • | | | • | • | • | |
| T7 | | | | | | • | | | • | | | |
| T8 | | | | | | • | • | | • | | | |
| T9 | | | | | | • | • | | • | | | |
| T10 | | | | | | • | • | | • | | | |
| T11 | | | | | | • | • | | • | | | |
| T12 | | | | | | • | • | | • | | | |
| L1 | | | | | | • | • | • | • | | | |
| L2 | | | | | | • | • | • | • | | | |
| L3 | | | | | | • | • | • | • | | | |
| L4 | | | | | | • | • | • | • | | | |
| L5 | | | | | | • | • | • | • | | | |
| S1 | | | | | | • | | • | • | | | |
| S2 | | | | | | • | | • | • | | | |
| S3 | | | | | | | | | | | | |
| S4 | | | | | | | | | | | | |
| S5 | | | | | | | | | | | | |

FIG. 2B

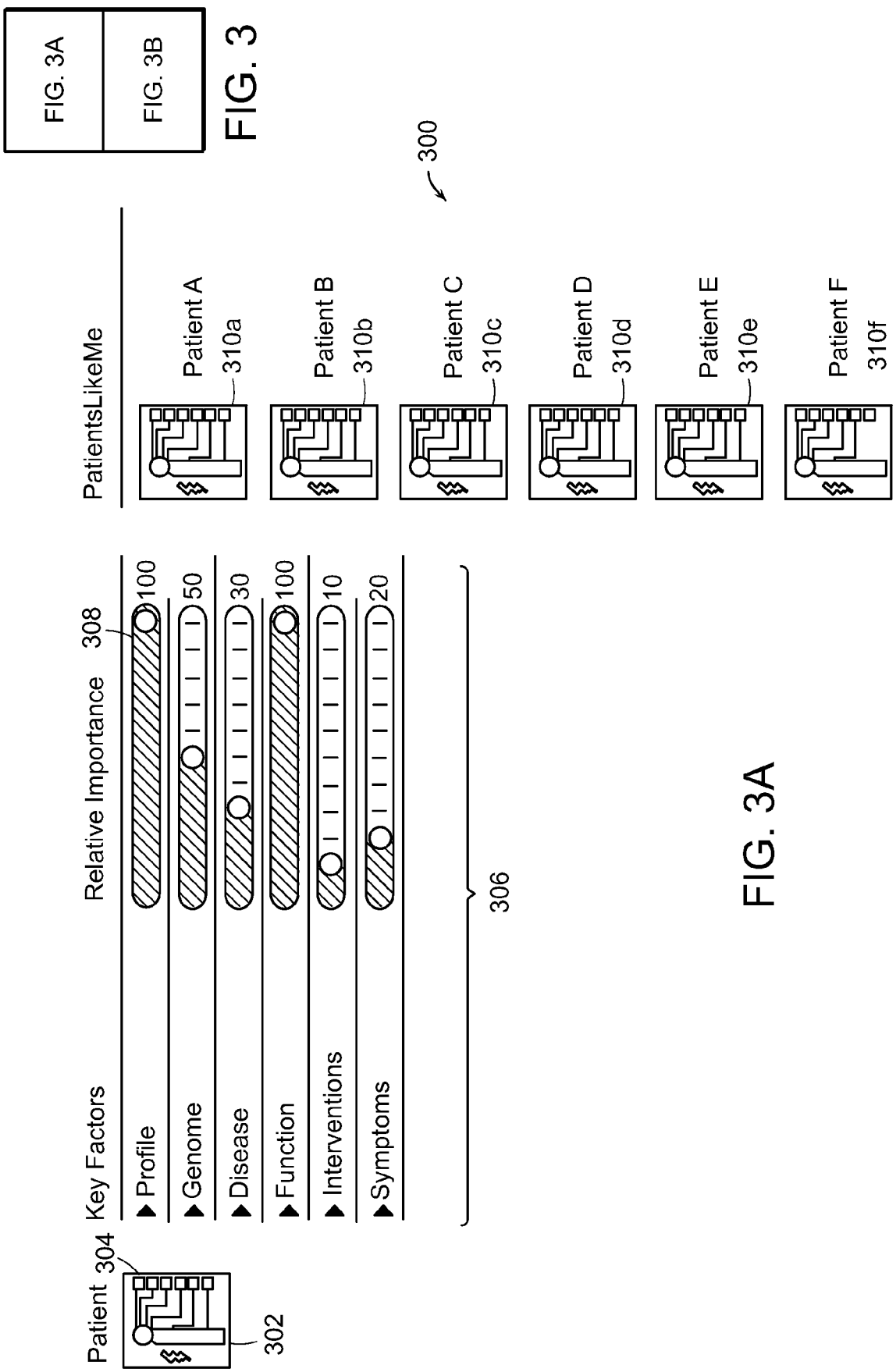

SELF-IMPROVING METHOD OF USING ONLINE COMMUNITIES TO PREDICT HEALTH-RELATED OUTCOMES

RELATED APPLICATION

This application is a continuation of PCT/US08/79674, filed on Oct. 12, 2008, and claims priority to U.S. Provisional Patent Application No. 60/998,669, filed on Oct. 12, 2007, U.S. Provisional Patent Application No. 60/998,768, filed on Oct. 12, 2007, and U.S. Provisional Patent Application No. 61/070,067, filed on Mar. 20, 2008. The entire contents of each of these applications is hereby incorporated by reference herein.

TECHNICAL FIELD

The present invention is directed to a method of using self-reported health data in online communities to predict significant health events in life-changing illnesses to improve the lives of individuals and to improve patient self-management.

BACKGROUND OF THE INVENTION

According to the World Health Organization, chronic diseases are now the major cause of disability and death worldwide, accounting for 59% of 57 million deaths annually and 46% of the global burden of disease. According to the U.S. Centers for Disease Control and Prevention, more than 90 million Americans live with chronic illnesses, accounting for more than 75% of the national $1.4 trillion bill for medical care costs. Chronic diseases also account for one-third of the years of potential life lost before age 65. Although widespread illnesses such as cardiovascular disease or diabetes are well-characterized in terms of risk-factors, prevention, and treatment, there are a host of under-researched and untreatable conditions; the National Organization for Rare Disorders (NORD) tracks approximately 6,000 rare disorders which, altogether, affect 23 million Americans.

Research into the relationship between health behavior and outcomes suffers from a variety of methodological flaws. There is often insufficient funding for prospective follow-up studies, service provision may be dependent on research staff, sample sizes are small, and particularly in the case of rare diseases, recruitment is difficult. Furthermore, results from clinical research tend to be written in scientific jargon, are difficult for the general public to understand, and refer to group averages rather than individual outcomes.

Accordingly, there is a need for an effective process to (i) collect data on interventions and health outcomes, (ii) model the likely course of a disease for an individual on the basis of their background and experience to-date, (iii) provide information on likely outcomes to the individual to help them manage their condition, and (iv) improve the model to improve the accuracy of predictions made.

The term "intervention" refers any event that has a positive, negative, or neutral effect on one or more medical conditions. The term intervention includes a variety of activities including, but not limited to, administration of a medication, administration of a remedy, administration of a nutritional supplement, administration of a vitamin, exercise, physical therapy, massage, stretching, consumption of food, rest, and sleep.

SUMMARY OF THE INVENTION

The present invention meets the foregoing need and provides an effective method of predicting health outcomes for an individual with a life-changing health condition, which will result in greater empowerment over their healthcare and better outcomes apparent from the discussion herein.

The invention provides a method for providing real-time personalized medical predictions for an individual patient. The method includes: providing a database containing patient information for a plurality of other patients including one or more attributes for each patient in the database; constructing a model of a disease based on disease progressions for the plurality of patients; receiving a request from the individual patient, the patient associated with one or more attributes; and making a real-time prediction for the individual patient based on the mode and the individual patient's attributes.

The one or more attributes can include at least one selected from the group consisting of: age, race, ethnicity, gender, height, weight, body mass index (BMI), body volume index (BVI), genotype, phenotype, severity of the disease, progression rate of the disease, measures of functional ability, quality of life, interventions, and remedies.

The disease can include at least one selected from the group consisting of: neurological diseases, Amyotrophic Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer blood cancer, fibromyalgia, epilepsy, post traumatic stress disorder, traumatic brain injury, cardiovascular disease, osteoporosis, chronic obstructive pulmonary disease, arthritis, allergies, autoimmune diseases, and lupus.

The data returned can include individual data for one or more members of the set of other patients. The data returned can include aggregate data for one or more members of the set of other patients. The method can include processing a request from the patient to view individual data.

The model can be based on data for a subset of the plurality of patients. The method can include processing a request from the patient to modify a composition of the subset of the plurality of patients. The composition of the subset of other patients can defined by fuzzy logic. The step of modifying the composition of the subset of the plurality of patients can include modifying the range of attributes of patients within the subset. The step of modifying the composition of the subset of the plurality of the patients can include modifying the importance of attributes of patients in composing the subset. The method can include conducting a multivariate pattern matching search of data related to the plurality of patients.

The method can include calculating a confidence interval for the prediction. The step of calculating a confidence interval for the prediction can include: selecting a set of reported data points from the plurality of other patients, for each of the reported data points in the set: obtaining a data set for the corresponding other patient to the reported data point calculating a predicted value with the data set and the model, and calculating an error between the predicted value and the reported data point; producing a distribution of the errors; and calculating a confidence interval from the distribution.

The set of reported data points can include n closest reported data points to the prediction. The set of reported data points can include reported data points within an ellipsoid defined by a distance metric. The size of the data set for the corresponding other patient can be comparable to a quantity of attributes associated with the individual patient.

The method can include analyzing an effect of an intervention by measuring a difference between a prediction absent the intervention and a reported outcome with the intervention. The difference can be measured for a plurality of individual patients. The difference can be compared to the distribution of error. The difference can be compared to the confidence interval for the model.

The method can include identifying one or more of the differences that exceed the confidence interval for the model. The method can include assembling a distribution of the differences for the plurality of individual patients, and computing a standard error for the distribution. The confidence interval can be calculated with a chi-square test. The confidence interval can be calculated from a measure of variance of the individual patient's attributes. The confidence interval can be calculated by comparing the individual patient's attributes to a model fit for the individual patient using the model.

The invention also provides a computer-readable medium whose contents cause a computer to perform a method for providing real-time personalized medical predictions for an individual patient. The method includes: providing a database containing patient information for a plurality of other patients including one or more attributes for each patient in the database; constructing a model of a disease based on disease progressions for the plurality of patients; receiving a request from the individual patient, the patient associated with one or more attributes; and making a real-time prediction for the individual patient based on the mode and the individual patient's attributes.

The invention also provides a method for providing real-time personalized medical predictions. The method includes: gathering patient-submitted information from a community of patients having a disease, the information including medical condition metrics and intervention data; utilizing the patient-submitted information to form a model of the disease; and predicting the progression of the disease in a particular patient by applying information submitted by an individual patient to the model.

The information submitted by the individual patient can include a date of onset of the disease. The step of predicting the progression of the disease can be performed in real time. The step of predicting the progression of the disease can include providing a confidence interval. The step of predicting the progression of the disease can include providing a graphical prediction. The graphical prediction can be a line chart depicting development of the disease with regard to a rating scale. The disease can include at least one selected from the group consisting of: neurological diseases, Amyotrophic Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer blood cancer, fibromyalgia, epilepsy, post traumatic stress disorder, traumatic brain injury, cardiovascular disease, osteoporosis, chronic obstructive pulmonary disease, arthritis, allergies, autoimmune diseases, and lupus. The model can be a model of the disease's pathology.

The invention provides a method for providing real-time personalized medical predictions for an individual patient. The method includes providing a database containing patient information for a plurality of patients including one or more attributes for each patient in the database; providing a graphical user interface displaying one or more attributes of the individual patient, the graphical user interface allowing the patient to formulate a search request specifying at least one of the attributes; searching the database of patient information for patients having the specified one or more attributes; providing a model of a disease based on disease progressions for the patients having the specified one or more attributes; and making a real-time prediction for the individual patient based on the model.

The one or more attributes can include at least one selected from the group consisting of: age, race, ethnicity, gender, height, weight, body mass index (BMI), body volume index (BVI), genotype, phenotype, severity of the disease, progression rate of the disease, measures of functional ability, quality of life, interventions, and remedies.

The disease can include at least one selected from the group consisting of: neurological diseases, Amyotrophic Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer blood cancer, fibromyalgia, epilepsy, post traumatic stress disorder, traumatic brain injury, cardiovascular disease, osteoporosis, chronic obstructive pulmonary disease, arthritis, allergies, autoimmune diseases, and lupus.

The data returned can include individual data for one or more members of the set of other patients or aggregate data for one or more members of the set of other patients. The method can include processing a request from the patient to view individual data. The method can also include processing a request from the patient to modify a composition of the set of other patients. The composition of the set of other patients can be defined by fuzzy logic.

The step of modifying the composition of the set of other patients can include modifying the range of attributes of patients within the set. The step of modifying the composition of the set of other patients can include modifying the importance of attributes of patients in composing the set. The method can include conducting a multivariate pattern matching search of data related to the other patients.

The outcome data can include at least one medical condition selected from the group consisting of: occurrence of epilepsy, occurrence of migraine, pain, fatigue, cognitive ability, anxiety, mobility, dexterity, and occurrence of allergies.

The method can include calculating a confidence interval for the model. The method can also include analyzing an effect of an intervention by measuring a difference between an expected outcome absent the intervention as predicted by the model and a reported outcome with the intervention. The difference can be measured for a plurality of individual patients. The difference can be a sum of the observational error rate based on a quality of the plurality of patient's pre-model data and a variation from the model. The difference can be compared to the confidence interval for the model.

The invention also provides a computer-readable medium whose contents cause a computer to perform a method for providing real-time personalized medical predictions for an individual patient. The method includes: providing a database containing patient information for a plurality of patients including one or more attributes for each patient in the database; providing a graphical user interface displaying one or more attributes of the individual patient, the graphical user interface allowing the patient to formulate a search request specifying at least one of the attributes; searching the database of patient information for patients having the specified one or more attributes; providing a model of a disease based on disease progressions for the patients having the specified one or more attributes; and making a real-time prediction for the individual patient based on the model.

The invention also provides a method for providing real-time personalized medical predictions. The method includes: gathering patient-submitted information from a community of patients having a disease, the information including medical condition metrics and intervention data; utilizing the patient-submitted information to form a model of the disease; and predicting the progression of the disease in a particular patient based on information submitted by an individual patient.

The step of predicting the progression of the disease can be performed in real time. The step of predicting the progression of the disease can include providing a confidence interval. The step of predicting the progression of the disease can include providing a graphical prediction. The graphical prediction can be a line chart depicting development of the disease with regard to a rating scale.

The disease can include at least one selected from the group consisting of: neurological diseases, Amyotrophic Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer blood cancer, fibromyalgia, epilepsy, post traumatic stress disorder, traumatic brain injury, cardiovascular disease, osteoporosis, chronic obstructive pulmonary disease, arthritis, allergies, autoimmune diseases, and lupus.

The invention also provides a method for providing personalized medical information comprising: providing a database containing patient information for a plurality of patients including one or more attributes for each patient in the database; providing a graphical user interface displaying one or more attributes of a patient, the graphical user interface allowing the patient to formulate a search request specifying at least one of the attributes; searching the database of patient information for patients having the specified one or more attributes; and returning data to the patient identifying a set of other patients having the specified one or more attributes.

The one or more attributes can include at least one selected from the group consisting of: age, race, ethnicity, gender, height, weight, body mass index (BMI), body volume index (BVI), genotype, phenotype, disease, disease severity, disease progression rate, measures of functional ability, quality of life, interventions, and remedies.

The database can include one or more correlations between an attribute and at least one secondary attribute selected from the group consisting of: quality of life, functional ability, pain, and treatment intensity.

The disease can include at least one selected from the group consisting of: Amyotrophic Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer blood cancer, fibromyalgia, epilepsy, post traumatic stress disorder, and traumatic brain injury.

The data returned can include individual data for one or more members of the set of other patients. The data returned can include aggregate data for one or more members of the set of other patients.

The method can include processing a request from the patient to view individual data. The method can also include processing a request from the patient to modify a composition of the set of other patients. The composition of the set of other patients can be defined by fuzzy logic. Modifying the composition of the set of other patients can include modifying the range of attributes of patients within the set. Modifying the composition of the set of other patients can include modifying the importance of attributes of patients in composing the set. The composition of the set of other patients can be defined by an optimal matching algorithm on a graph of attribute similarity metrics. The composition of the set of other patients can be defined by a scalar-vector decomposition on a matrix of similarities of attributes of the set of other patients. The method can also include conducting a multivariate pattern matching search of data related to the other patients.

The invention also provides a computer-readable medium whose contents cause a computer to perform a method for providing personalized medical information. The method includes the steps of: providing a database containing patient information for a plurality of patients including one or more attributes for each patient in the database; providing a graphical user interface displaying one or more attributes of a patient, the graphical user interface allowing the patient to formulate a search request specifying at least one of the attributes; searching the database of patient information for patients having the specified one or more attributes; and returning data to the patient identifying a set of other patients having the specified one or more attributes.

The invention also provides a method for providing personalized medical information. The method includes the steps of: providing a database containing patient information for a plurality of patients including one or more attributes for each patient in the database; providing a graphical user interface displaying one or more attributes of a patient, the graphical user interface allowing the patient to formulate a search request specifying at least one of the attributes; searching the database of patient information for patients having the specified one or more attributes; and providing outcome data for other patients that previously had similar attributes to the specified one or more attributes.

The one or more attributes can include at least one selected from the group consisting of: age, race, ethnicity, gender, height, weight, body mass index (BMI), body volume index (BVI), genotype, phenotype, disease, disease severity, disease progression rate, measures of functional ability, quality of life, interventions, and remedies.

The disease can include at least one selected from the group consisting of: Amyotrophic Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer, blood cancer, fibromyalgia, epilepsy, post traumatic stress disorder, and traumatic brain injury.

The data returned can include individual data for one or more members of the set of other patients. The data returned can include aggregate data for one or more members of the set of other patients.

The method can also include processing a request from the patient to view individual data. The method can also include processing a request from the patient to modify a composition of the set of other patients. The composition of the set of other patients can be defined by fuzzy logic. Modifying the composition of the set of other patients can include modifying the range of attributes of patients within the set. Modifying the composition of the set of other patients can also include modifying the importance of attributes of patients in composing the set.

The method can also include conducting a multivariate pattern matching search of data related to the other patients. The outcome data can include at least one medical condition selected from the group consisting of: occurrence of epilepsy, occurrence of migraine, pain, fatigue, cognitive ability, anxiety, mobility, dexterity, and occurrence of allergies.

The invention also provides a computer-readable medium whose contents cause a computer to perform a method for providing personalized medical information. The method can include: providing a database containing patient information for a plurality of patients including one or more attributes for each patient in the database; providing a graphical user interface displaying one or more attributes of a patient, the graphical user interface allowing the patient to formulate a search request specifying at least one of the attributes; searching the database of patient information for patients having the specified one or more attributes; and providing outcome data for other patients that previously had similar attributes to the specified one or more attributes.

Accordingly, a method of modelling an individual's disease progression using an online community can include the steps of creating an online community for people with life-changing illnesses; creating membership accounts for patients joining the online community; receiving personal and medical information from the patient; categorizing and storing the received personal and medical information to a member database; modelling the relationship between an individual's background and current health status in comparison to data received from other patients like them; making predictions about future outcomes which are presented to the patient with levels of confidence; allowing predictions to be modified on the basis of received information from health providers or administrative records systems, such as utilization of health services, laboratory test results, diagnostic procedures, therapeutic procedures, or from other measurement systems of phenotypic or genotypic characteristics; and receiving feedback from members over the course of time to validate or modify the model accordingly in order to improve the model.

The present invention also provides a method of displaying visual information to a patient about their likely predicted disease states, health events, and health outcomes which includes estimations of confidence surrounding the likelihood of such outcomes, which can change over time in response to more data from themselves, from other sources such as health providers or administrative systems, or other members of the site.

The invention also provides a method of grouping patients by background and illness-specific characteristics including but not limited to: the presence or absence of a genetic mutation; the presence or absence of a genetic polymorphism; the presence of absence of a pattern of familial inheritance apparent from a family history; the presence or absence of a known or unknown proteome sequence; the staging of disease progression according to self-report or assessment by a healthcare professional; functional outcome assessed by a self-report questionnaire or by a healthcare professional; demographic information submitted by the patient including, but not restricted to age, sex, ethnicity, socio-economic status, health behaviours, diet, exercise, smoking history, drug use, surgical history, past and present geographical location, personality, and/or chance; and the rate, nature, direction of change, or interaction of any of the above. The method of grouping can include but is not limited to multiple regression to identify significant predictor variables such as suggested above.

The present invention also provides a method by which the grouping of patients permits the construction of a mathematical model establishing the likelihood of important medical outcomes such as, without limitation, when a patient may need a health intervention (e.g., surgery, tablet, therapy, assistive technology, home modification, nutritional supplement, lifestyle change and the like); the likelihood of adverse events in response to intervention (e.g., side effects, injuries, death and the like); the likelihood that the patient will develop a symptom, condition, or disease; the likelihood that a child or other relative of the patient will develop a symptom, condition, or disease; the likelihood that a patient will need to receive care in an institution as opposed to receiving care at home; the point at which the costs of paying for medical care will achieve a certain level; and the degree of improvement which might be experienced if the patient chooses to start a given intervention.

The present invention also includes a method by which a predicted event is displayed on the patient's medical profile at a future data, such as the events as noted above. The predicted event may also be presented with a level of confidence dependent on the quantity and quality of data entered by the user or by data available from other sources and users of the system.

The present invention also includes a method by which models used to predict future events are strengthened or weakened by ongoing feedback from users once the predicted event has come to pass.

The present invention also provides a server for facilitating a Web site portal that collects and analyzes information related to patients having at least one common characteristic such as a disorder, wherein the server communicates with clients via a distributed computing network and the patients and related caregivers can access the Web site portal via a client, and wherein the server comprises: (a) a memory storing an instruction set and historical data related to a plurality of patients; and (b) a processor for running the instruction set, the processor being in communication with the memory and the distributed computing network, wherein the processor is operative to: (i) receive additional data related to the patients and add the additional data to the historical data; (ii) model the historical data generally for a subset of the patients with a second common characteristic; (iii) model the historical data for an individual patient within the subset of the patients; (iv) make a prediction of a timeframe for a future event based on the modelled subset and individual patient historical data; (v) add the prediction to the historical data; (vi) analyze the prediction based on the historical data to determine a confidence parameter; and (vii) provide a display of the historical data modelled for the subset, the historical data modelled for the individual patient, the prediction for the individual patient, and the confidence parameter.

It should be appreciated that the present invention can be implemented and utilized in numerous ways, including without limitation as a process, an apparatus, a system, a device, a method for applications now known and later developed or a computer readable medium. These and other unique features of the system disclosed herein are readily apparent from the subject description and the accompanying disclosure and drawings.

BRIEF DESCRIPTION OF THE DRAWINGS

For a fuller understanding of the nature and desired objects of the present invention, reference is made to the following detailed description taken in conjunction with the accompanying drawing figures wherein.

DEFINITIONS

Figure 1:
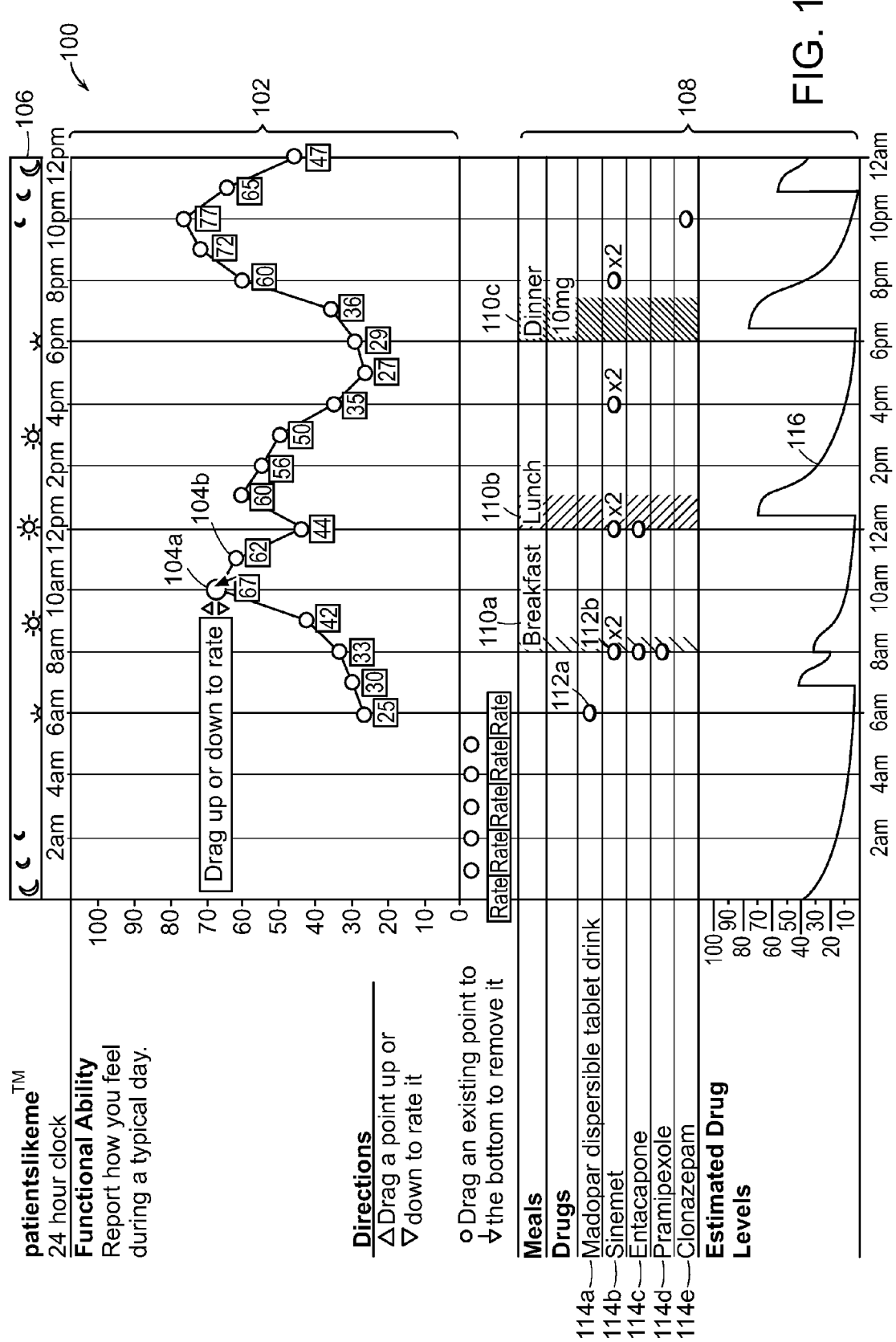
FIG. 1 is a diagram depicting an exemplary graphical element.

The instant invention is most clearly understood with reference to the following definitions:

As used in the specification and claims, the singular form "a," "an," and "the" include plural references unless the context clearly dictates otherwise.

The term "disease" refers to an abnormal condition of an organism that impairs bodily functions. The term disease includes a variety of physical ailments including, but not limited to, neurological diseases (e.g., Amyotrophic Lateral Sclerosis (ALS), Multiple Sclerosis (MS), Parkinson's Disease), Human Immunodeficiency Virus (HIV), Acquired Immune Deficiency Syndrome (AIDS), cancers (e.g., bladder cancer, blood cancer, breast cancer, colorectal cancer, endometrial cancer, leukemia, lung cancer, lymphoma, ovarian cancer, pancreatic cancer, prostate cancer, and skin cancer), diabetes, digestive disorders (e.g., irritable bower syndrome, gastro esophageal reflux disease, and Crohn's Disease), cardiovascular diseases, osteoporosis, chronic obstructive pulmonary disease (COPD), arthritis, allergies, geriatric diseases, and autoimmune diseases (e.g., lupus). The term disease also include mental ailments including, but not limited to, depression, anxiety disorders, post traumatic stress disorder, mood disorders, psychotic disorders, personality disorders, and eating disorders.

The term "medical condition" refers to a manifestation of a disease such as a symptom. For example, if a patient suffers from Amyotrophic Lateral Sclerosis (ALS), the patient may experience one or more medical conditions such as dysphagia (impaired swallowing).

Detailed Description Of The Invention

The invention is directed, in part, to method of using self-reported health data in online communities to predict significant health events in life-changing illnesses to improve the lives of individuals and to improve patient self-management.

Data Acquisition

Self-reported health data can be gathered from a number of sources such as the PatientsLikeMe™ service available at www.patientslikeme.com.

An online community can be created to allow patients to contribute information about themselves, their diseases, their medical conditions, and their interventions. Each patient can register for one or more communities focused on a particular disease. For example, a patient can join an ALS community. As part the registration process, the patient can enter various demographic and/or medical information. Exemplary information can include: age, race, ethnicity, gender, height, weight, body mass index (BMI), body volume index (BVI), genotype, phenotype, disease, disease severity, disease progression rate, measures of functional ability, quality of life, interventions, remedies, and medical data such as tests. Patient information can also include historical or environmental data such as weather data for the patient's environment (e.g., temperature, humidity, pollen count, air quality) and the patient's past exposure to the sun. Patient information can also include personality information. Personality information can be represented by varius classification systems such as the DISC assessment, Enneagram of Personality, Keirsey Temperment Theory, and the Meyer-Briggs Type Indicator. Genotype can be determined through known SNP (single nucleotide polymorphism) or full-genome sequencing techniques.

After registration, the patient periodically inputs information about one or more medical conditions and one or more remedies. For example, an ALS patient can indicate when she sleeps, eats, and takes various medications such as riluzole. Likewise, the ALS patient can enter data on their functional ability at various times throughout the day. Rating scales for assessing ALS patients include the Appel ALS rating scale and the ALS Functional Rating Scale.

Referring to FIG. 1, user interface 100 includes a medical condition metric portion 102, which allows the patient to input a medical condition metric (in this example, the patient's functional ability). The user can place multiple data points 104 in the medical condition metric chart, which includes a time scale. Data points 104 can be adjusted with respect to time and/or magnitude. For example, if the patient is indicating how she feels now or at a designated time, the patient can be limited to moving data point 104 up or down. Alternatively, the patient can input data for a time by dragging the data point to the left or right. The patient can be restricted in some embodiments from setting a data point in the future.

User interface 100 also includes an intervention portion 108. Intervention portion 108 allows the patient to record one or more interventions such as administration of a medication, administration of a remedy, administration of a nutritional supplement, administration of a vitamin, exercise, physical therapy, massage, stretching, consumption of food, rest, and sleep. For example, the patient can designate when meals are eaten by adjusting bars 110a, 110b, and 110c to indicate the beginning and ending of the meal. Likewise, the patient can indicate when one or more drugs 114a-114e are administered by placing markers 112 (which may depict pills) on a time scale.

Various types of remedies can be scheduled for specific times. For example, the patient can be prescribed to take madopar at 6 A.M. In this situation, user interface 100 can display a medication schedule. The patient can modify this schedule to reflect the actually administration by dragging marker 112a. Likewise, the patient can indicate that the drug was consumed by clicking on the marker 112a. Clicking on the marker can change the appearance of the marker 112a (e.g., its color) and thus can be used by patients, particularly patients with memory problems, to more faithfully follow a medication program.

User interface 100 can also include pharmokinetic data, such a pharmokinetic curve 116 that depicts the concentration of a medication within the patient over time. Multiple pharmokinetic curves 116 can be depicted in various colors or patterns to reflect varying pharmokinetic properties of various medications.

This patient information is then stored in various formats. The data can be stored in a relational database. Suitable relational databases includes DB2® and INFORMIX® both available from IBM Corp. of Armonk, N.Y.; MICROSOFT JET® and MICROSOFT SQL SERVER® both available from the Microsoft Corp. of Redmond, Wash.; MYSQL® available from the MySQL Ltd. Co. of Stockholm, Sweden; ORACLE® Database, available from Oracle Int'l Corp of Redwood City, Calif.; and SYBASE® available from Sybase, Inc. of Dublin, Calif. Additionally or alternatively, the data can be stored in a state model.

A Priori Disease Modelling Algorithms

The invention also provides an a priori method for modelling diseases. This method can include an a priori model of a progressive disease. This method does not rely on an underlying description of a pathology, and thus may be used even for diseases for which a pathology is unknown.

The model allows for the prediction of the state of a disease at some point in time (e.g., past, present, and future) based on data provided by an individual patient. The data can be any of the items discussed herein, including, but not limited to medical condition metrics (e.g. rating scales) and the date of onset of the disease. The model is designed to provide an accurate and reliable prediction even where the data provided by the individual patient and the community of patients is heterogeneous (e.g., reported at varying time intervals).

This model describes the state of a disease for a patient at any point in time as a scalar-valued or vector-valued function. For example, in a model of ALS, the state can be an integer value in the closed interval between 0 and 48 (the range of the overall Amyotrophic Lateral Sclerosis Functional Rating Scale-Revised (ALSFRS-R) scale) or the state can be a twelve-dimensional vector indicating the responses to all twelve ALSFRS-R questions. The ALSFRS-R is a 48-point scale including an questions assessing the patient ability to walk, breath, communicate, etc.

The progression of a disease can be described by the time required since some event (e.g. onset or diagnosis of the disease) to reach some value in the above-described disease state function. It may also be described as a differential equation or as the time required to cross some boundary in the state space. This progression can be held constant for any particular patient (and thus be treated as an inherent attribute of the patient's disease) or it can be variable over the course of the disease.

Using the progression rate as one dimension, a multivariate function may describe set of all patients in a population. The population can include a group of patients, for example, all patients participating a community such as those provided through the PatientsLikeMe™ service. Each patient is associated with a set of data points describing their disease state at different points in time. In the above example of a scalar-valued disease state function (overall ALSFRS-R score), the function would exist as a surface (scalar function) of two dimensions: (i) progression rate and (ii) time since some event (e.g. onset of the disease). In the example of a vector-valued disease state function, the function would be a twelve-dimensional vector field as a function of two dimensions ($f(R^2) \rightarrow R^{12}$).

An expression of this model function can be determined using numeric methods such as the Levenberg-Marquardt algorithm to provide an optimal fit according to some appropriate choice of function. The Levenberg-Marquardt algorithm is described in publications such as Donald Marquardt, *An Algorithm for Least-Squares Estimation of Nonlinear Parameters,* 11 SIAM Journal on Applied Mathematics 431-41 (1963). For example, a scalar bi-cubic function of time and progression rate can provide a good functional form to describe a change in overall ALSFRS-R score over time.

The fitness of the model may be improved through an iterative procedure whereby several first-generation parameters are replaced with second-generation variants. For example, the initial value of progression rate can be replaced for each patient in the data set with a value that provides a least-mean-squares fit to the model. Thus, the initial approximation of progression rate is improved by iteration. The model function can then be re-fit to the new set of parameters and this process can be repeated one or more times, until some stopping conditions (e.g. convergence or lack of further change in the progression rates) are met.

A set of error bounds, or a confidence interval, can be determined from the actual error rate of the model. To determine the error bounds around a particular prediction (i.e., a prediction that a specific patient will have a certain disease state at a specified time), the method can consider all known patient-reported data points within a certain radius of the prediction, or alternatively, the n nearest patient-reported data points for some positive integer n. In either case, a valid definition of radius (distance metric) can be derived from the patient's progression rate or the derivative of the model at the prediction, relating change in one dimension (time) to change in another dimension (e.g. overall FRS score). This rate of change defines the shape of an ellipsoid, and thus a distance metric, around the prediction.

Consequently, the set of nearby patient-reported data points may be used to compute a distribution of errors. For each patient-reported data point in this set, the corresponding patient is identified and fit into the model as if they only had as many data points as the patient being predicted (that is, the patient around whose prediction the confidence interval is being evaluated). The disease state at the time corresponding to the patient-reported data point is then predicted from this patient, and the error (difference between the prediction and the actual, uncensored data point) is evaluated. This set of errors produces a distribution, and a desired confidence interval (e.g., a 95% confidence interval) can be computed by evaluating the distribution (e.g., the mean error $\pm 1.96$ $\sigma$ (standard deviations)). This confidence interval about a particular prediction can be transformed into an overall set of confidence bands around the model for a particular patient by evaluating the error distribution about a set of time-values. The confidence interval can be smoothed by fitting the confidence values to some linear or nonlinear function of time, producing confidence bands that are less sensitive to areas of the model space where there are fewer known data points.

Figure 4:
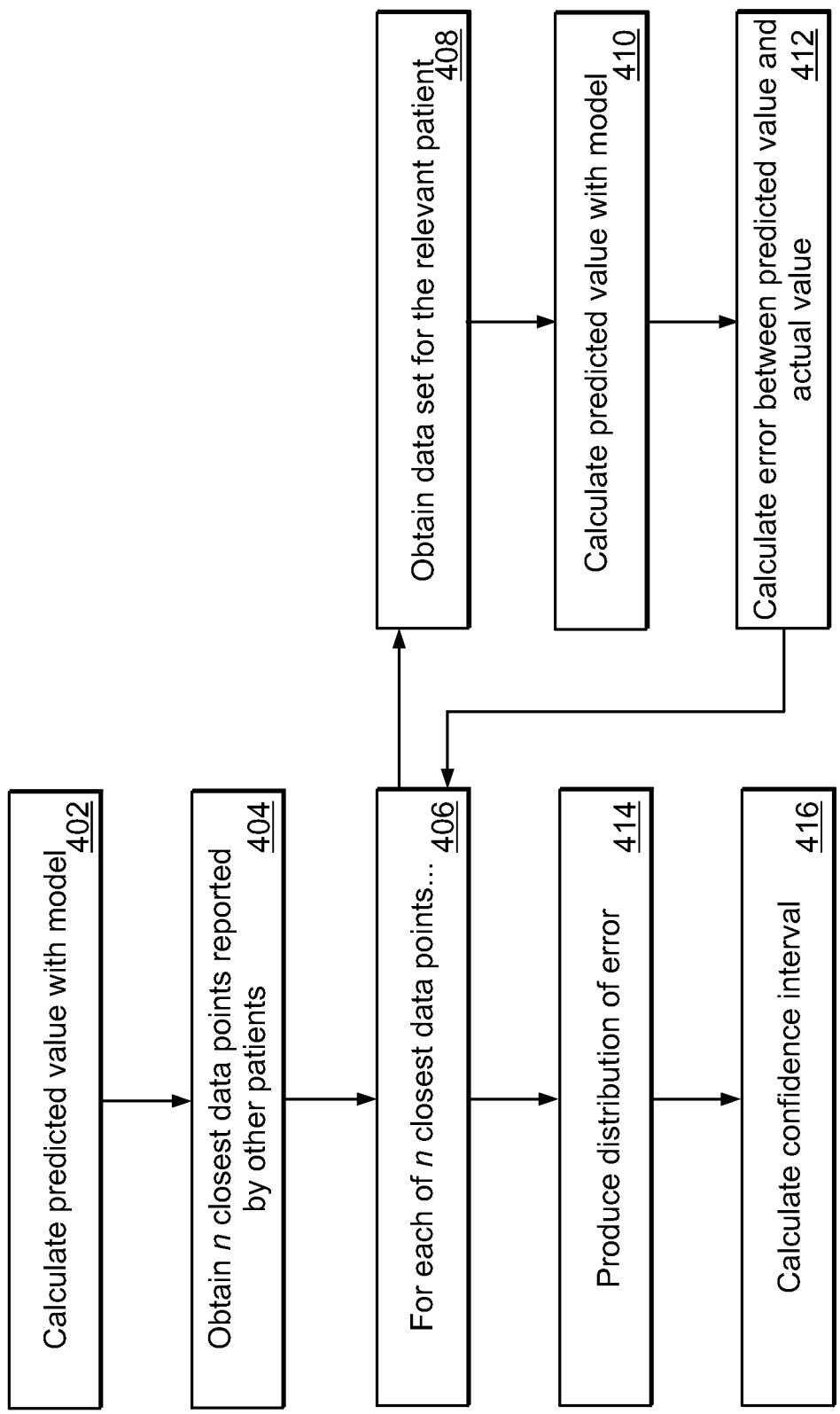
FIG. 4 is a diagram depicting a method of producing a confidence interval for a predictive model.

This method is further explained with reference to FIG. 4. In step 402, a predicted value is calculated for a specific patient using the models described herein In step 404, the n closest data points reported by other patients are then retrieved. For each of these data points (step 406), a data set is obtained in step 408 from the relevant patient (i.e. the patient who previously reported the data point selected in step 406). This data set can be limited to the number of data points available for the specific patient. For example, if the specific patient has entered 50 data points, only 50 data points will be retrieved for each of the other patients, regardless of how many data points may be available. The use of a comparably sized data set permits an accurate estimation of error based on similar conditions. Each data set is used to calculate a predicted value with the model (step 410). In step 412, the error between the predicted value and the actual patient-reported value is calculated. In step 414, a distribution of error is assembled. This distribution of error is then used in step 416 to calculate a confidence interval.

Figure 5:
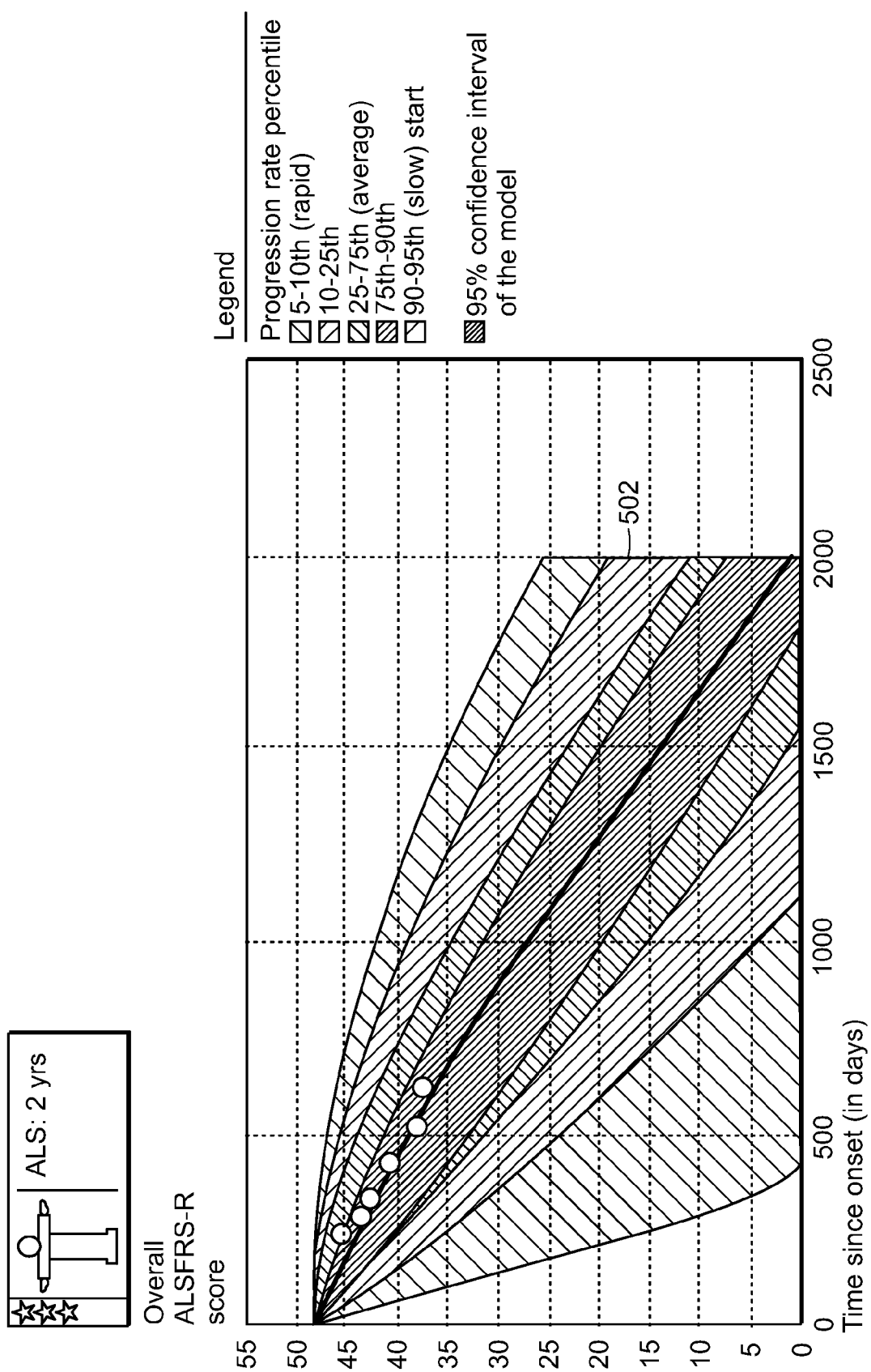
FIG. 5 is a diagram depicting an exemplary graphical element displaying a prediction and a confidence interval.

This confidence interval can be represented graphically as depicted by shading 502 in FIG. 5 and may also be used to evaluate the significance of disease interventions.

In addition, the efficacy of a specific treatment can be evaluated based upon examining the disease state (e.g., the ALSFRS-R score) for a set of patients receiving that treatment and comparing the disease state to the expected model state in the absence of such treatment. Efficacy of the treatment may be expressed as a change in the disease state metric responses (e.g., "mean of five point greater ALSFRS-R score than expected at six months") or as a change in the progression rate (e.g., "median twenty percent less loss of function at four months").

Pathological Disease Modelling Algorithms

The invention also provides a pathological modeling algorithms for a disease, which relies on an understanding of the underlying pathology of the disease, and can be used to make predictions about a subset of a population or about an individual.

Figure 6:
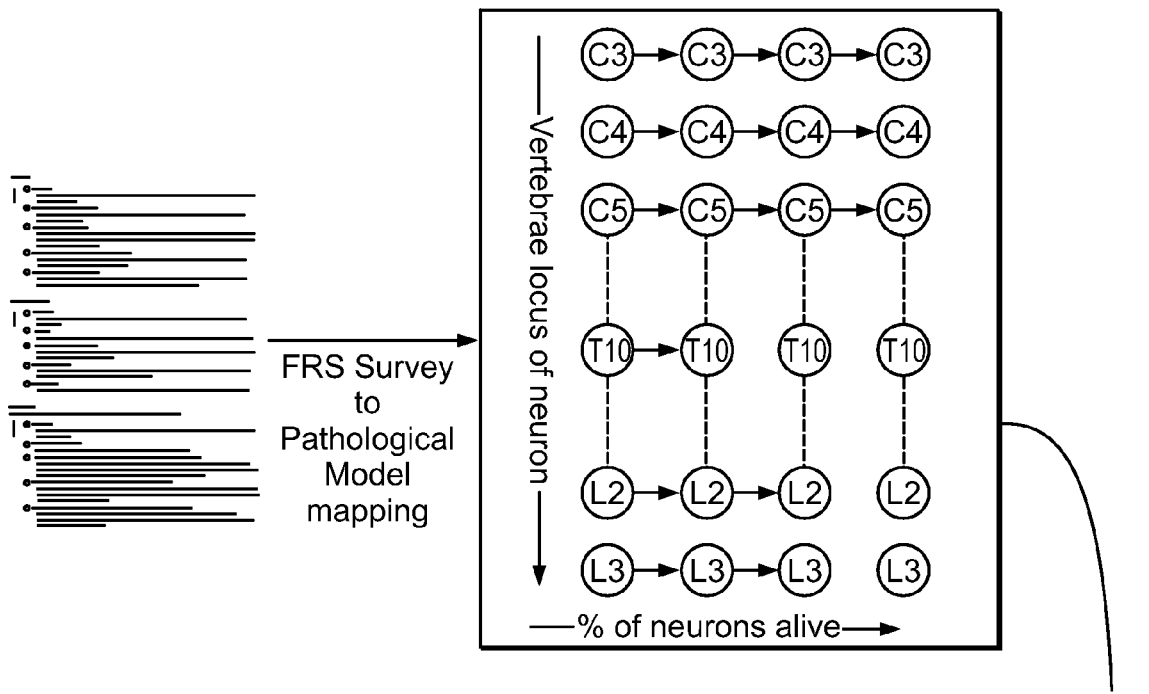
FIG. 6 is a diagram depicting the construction of a pathological model of ALS from the ALSFRS questionnaire, the progression of the pathological model, and the use of the pathological model to predict answers on a future ALSFRS questionnaire.
Figure 6:
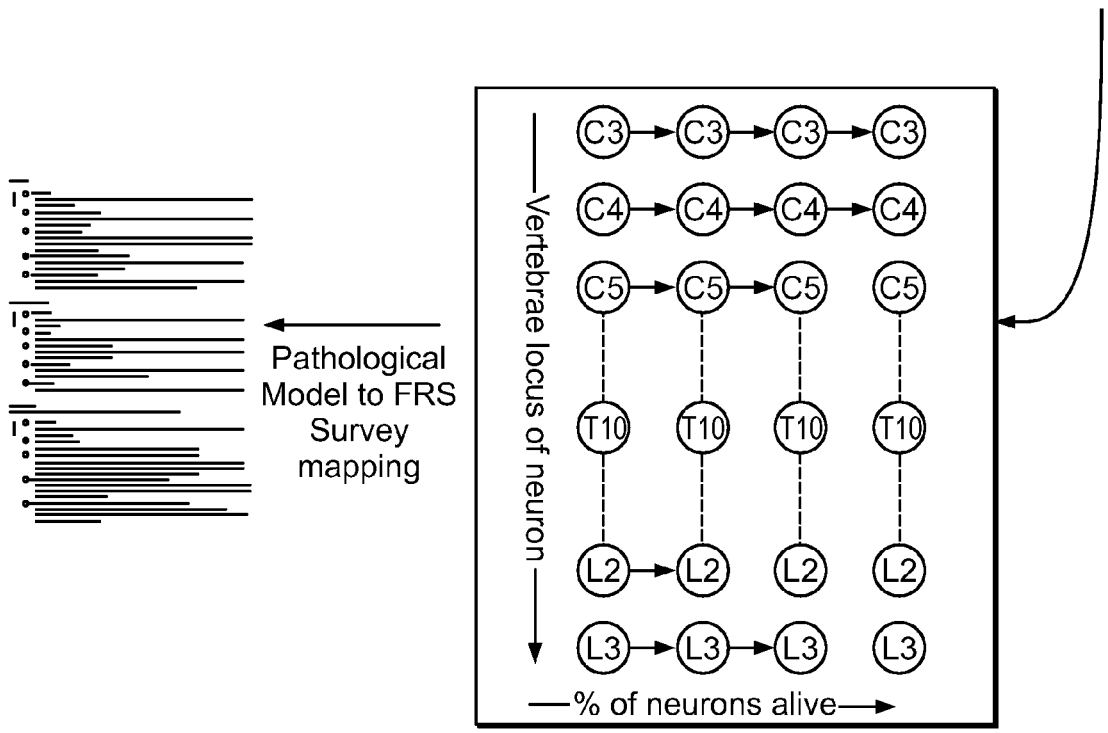

This model describes the state of the disease for some patient at any point in time as a simplified pathological model. For example, in ALS, a finite array representing motor neurons along the spinal cord and degrees of neuron death can serve as the pathological model, as depicted in FIG. 6.

For Traumatic Brain Injury (TBI), a connected graph representing regions of the brain and damaged connections (weights on the edges of the graph) or damaged regions (values of the nodes of the graph) can serve as the pathological model.

Figure 2A:
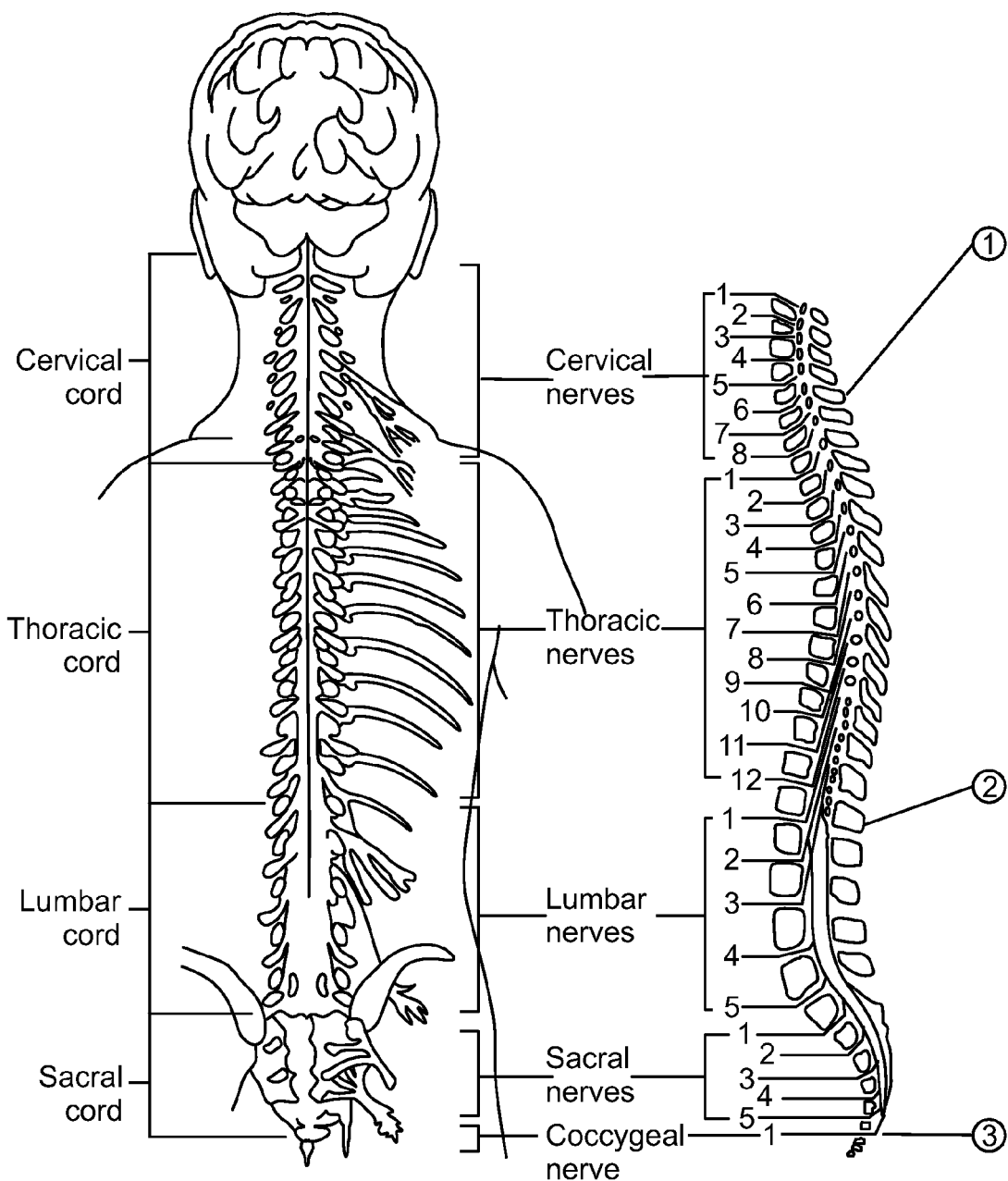
FIG. 2 is a diagram depicting the mapping of the ALSFRS scale to specific spinal nerves.

This model relies on a bidirectional mapping between some user-provided data set and the pathological model. For example, as depicted in FIG. 2, individual questions in the ALSFRS-R or ALSFRS-EX (generically, ALSFRS) can be mapped to individual vertebra regions, and thus a description of the specific damage to the motor neurons can be derived from a set of ALSFRS responses. Similarly, a modeled state of the motor neuron damage may be mapped back to a set of ALSFRS responses.

Similarly, in TBI, individual questions in the Craig Handicap Assessment and Reporting Technique (CHART), the Disability Rating Scale (DRS), the Level of Cognitive Functioning Scale (LCFS), and other published surveys can be used individually or in combination and may be mapped to specific regions of brain trauma or damage.

The mapping can be achieved by establishing an association between individual components (neurons, brain regions, cell types, protein pathways, organs, or other physiological components, depending on the disease) to observable functional or diagnostic effects as communicated by a patient survey, a caregiver survey, laboratory test results as communicated by the patient or a caregiver, or other data provided by the patient or a caregiver. The associations can be established based on existing published or as-yet-unpublished literature, laboratory experimentation, or existing physiological models.

The progression or treatment of the disease can be modeled by establishing factors for the change of the pathological model. For example, in ALS, a set of ALSFRS responses may map to the motor neurons along a certain set of vertebrae being fifty percent functional. Another set of ALSFRS responses may map to those same motor neurons being ten percent functional, and another set being forty percent functional. Based upon a set of these associations, derived from a set of patients used as a training set, data about such population being obtained via a set of surveys on a web site, entry via handheld devices, or other means, a dynamic model can be developed. For example, as depicted in FIG. 6, in ALS, a Markov model or Hidden Markov model can be trained using the Baum-Welch algorithm to determine an optimal transition matrix describing the decay of neurons in the pathological model. The Baum-Welch algorithm is described in publication such as Leonard E. Baum et al., *A Maximization Technique Occurring in the Statistical Analysis of Probabilistic Functions of Markov Chains*, 41(1) Ann. Math Statist. 164-71 (1970). Additionally or alternatively, a genetic algorithm can be invoked to determine optimal rates of decay of neurons in the pathological model in ALS, or to determine rates of functional adaptation due to retraining of regions of the brain in TBI.

As discussed above, and in the context of FIG. 4, a confidence interval can be determined from the actual error rates of the model. To determine the error bounds around a particular prediction, all known patient outcomes (and thus, associated pathological states) within a certain radius of the prediction can be considered, or alternatively, the n nearest patient-reported outcomes for some positive integer n. In either case, a valid definition of radius (distance metric) can be derived from the change weights or transition probabilities of the model.

Consequently, the set of nearby patient-reported outcomes can be used to compute a distribution of errors. For each patient-reported data point in this set, the corresponding patient is identified and fit into the model as if they only had as many data points as the patient being predicted (i.e., the patient around whose prediction the confidence interval is being evaluated). The disease state at the time corresponding to the patient-reported data point is then predicted from this censored patient, and the error (difference between the prediction and the actual, uncensored data point) is evaluated. This set of errors produces a distribution, and a desired confidence interval (e.g., a 95% confidence interval) can be computed by evaluating the distribution (e.g., the mean error $+/-1.96$ standard deviations). This confidence interval about a particular prediction can be transformed into an overall set of confidence bands around the model for a particular patient by evaluating the error distribution about a set of time-values. The confidence interval can be smoothed by fitting the confidence values to some linear or nonlinear function of time, producing confidence bands that are less sensitive to areas of the model space where there are fewer known data points.

This confidence interval can be represented graphically as depicted in FIG. 5 and can also be used to evaluate the significance of disease interventions.

Such a model of disease progression, coupled with such a bidirectional mapping to functional responses or descriptions of the disease, can be used to make predictions as to not only the general course of the disease, but also as to the expected need for (or probability of need for) particular interventions, or the probability of a patient experiencing specific symptoms or outcomes. For example, in ALS, the probability that a patient will need a wheelchair, or a vent, or a feeding tube, can be expressed over time (see FIG. 3 herein). Alternatively, the point in time at which a patient will most likely need an intervention such as one of these, subject to some confidence interval, can be predicted.

In addition, the efficacy of a specific treatment can be evaluated based upon inferring the state of the pathological model (based upon observing the functional or diagnostic responses) for a set of patients receiving that treatment and comparing the model state to the expected model state in the absence of such treatment. Efficacy of the treatment can be expressed either as a change in the pathological model (e.g., "twenty percent reduction in the rate of neuron degradation over a period of four months") or as a change in the resulting functional, symptomatic, or diagnostic responses (e.g., "thirty percent extension in the median time to requiring the use of a wheelchair").

Data Correction

Another example of this iterative improvement to the model is to correct for the time offset for each patient. Depending on the disease and the specifics of the model, patients may be reporting their date of onset incorrectly due to improper recollection, the imprecise definition of 'first symptom', or the fact that some disease variants may have more obvious first symptoms than others. A correction offset to the onset date for each patient (effectively adding Q to the time value of each data point, where Q is some real-valued number) may reduce the least-mean-squares error of the model. Given that the patient's corrected onset date must be before the date of diagnosis, the optimization for Q may be performed on some bounded interval, e.g., $Q=\{q \in R: q \geq -d, q \leq d\}$ where d is the time interval between stated onset and diagnosis. This optimization may be performed using a numerical method such as Brent's method. Brent's method is discussed in publications such as R. P. Brent, *Algorithms for Minimization without Derivatives* (1973). The model function can be re-fit to the new set of parameters in this instance as well, and this process can be repeated one or more times, until some stopping conditions (e.g. convergence, or lack of further change in the value of Q) are met.

Additionally, missing data algorithm (including regression or expectation maximization (EM) algorithms) can be used to generate complex datasets for fitting. These datasets include flags for imputed values to allow sensitivity analyses that estimate the impact of missing value imputation on model-based forecasts and predictions.

Model Improvement

Exploratory data analysis techniques can be utilized to explore which variables and combinations of variables are associated with the response (outcome, event, disease state) of interest. A sample, or training dataset is analyzed using simple multiple regression methods (in small, well-behaved samples) or exploratory methods for very large datasets, with or without missing values. In one example, the CHAID (CHi-squared Automatic Interaction Detector) method, involves analyzing and ordering every possible combination of attributes. The analyst guides the analysis via parameter settings in the CHAID algorithms to identify which attribute is the most important predictor, which attributes have no predictive value, and how attributes combine or interact together to help in prediction of the response.

In cases where groups of patients are expected to have different response processes (i.e., where different variables are influencing and determining responses) cluster analysis methods may be used to optimize group identification and assignment. Both agglomerative (bottom-up) and divisive (top-down) clustering algorithms, with control over distance measures (which guide the measurement of similarity of the cases being considered for group assignment), can be used.

Linear statistical models, such as logit, probit, and proportional hazards can be utilized to produce forecasts and estimated responses.

Model fit can be improved through the use of Neural Networks, or non-linear statistical models of response. These models are appropriate for pattern recognition and modeling when clusters of processes and sub-processes must be taken into account to optimize forecasts and estimates of response.

Prediction of Disease Progression:

The disease modelling algorithms herein can be used to provide personalized predictions of a particular patient's experience. For example, upon diagnosis with a disease, the patient can enter information about the themselves, the disease, and one or more medical conditions. This information is then fed into the algorithms to determine where the patient is along the progression of a disease. For example, as depicted in FIG. 6, the algorithms can predict what an ALS patient's ALSFRS-R value will be at a give point in the future. Likewise, the algorithms can predict when certain events will occur, such as confinement to wheel chair or use of a ventilator. Such predictions can be presented to the patient with estimations of confidence in the prediction.

Figure 3B:
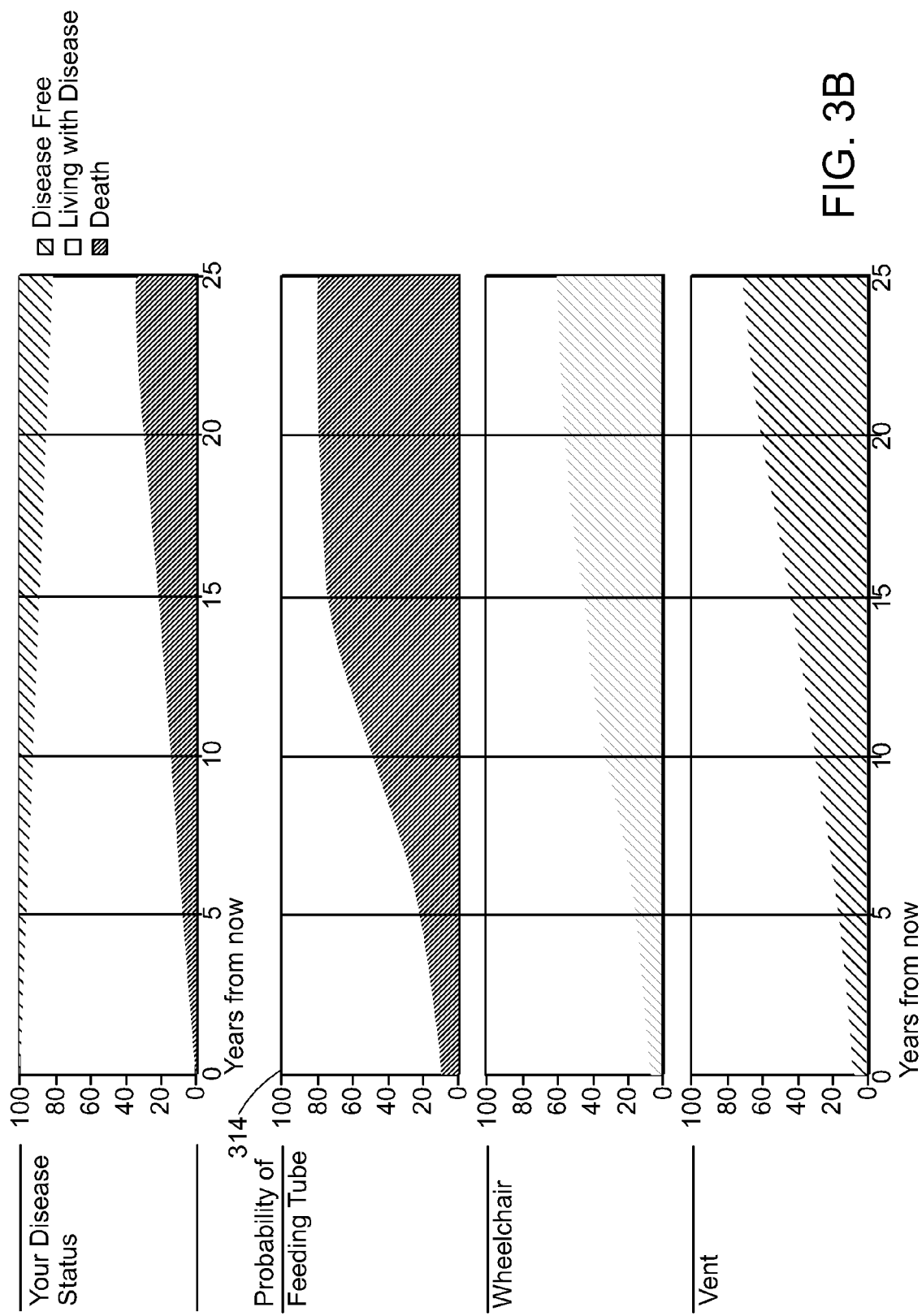
FIG. 3 is a diagram depicting an exemplary user interface for viewing and refining a group of similar patients and prediction of disease progression.

Referring to FIG. 3, an exemplary user interface 300 is provided for viewing and refining a prediction of disease progression. An icon 302 represents the patient controlling the system. The icon 302 includes several color-coded boxes 304, which represent the status of various body systems or regions (e.g., the legs, the spine, and the eyes).

The user interface 300 also includes a population chooser interface 306 for refining the prediction by expanding or contracting the population on which the prediction is made. For example, a patient can initially view a prediction based on all patients within a community (e.g. all patients with ALS). The patient can then alter one or more parameters such as age, gender, race, ethnicity, genotype, etc. The predictions can be updated in real time as the population is altered. In the depicted example, the user can alter the population by sliding one or more sliders 308 to adjust the relative importance a factor such as profile (e.g., age, gender, race, ethnicity, socioeconomic status), genome, disease, function (e.g., as assessed by the ALSFRS-R scale), interventions (e.g., medications consumed), and symptoms (e.g., dysphagia).

The user interface 300 can display icons 310$a$-310$f$ for one or more patients that are similar to the patient. Icons 310 can be updated as the patient alters the population using population chooser interface 306. The patient can "drill down" to view specific details and profiles of one or more patients, for example, by clicking on one of the icons 310.

The user interface 300 can also include one or more charts 312, 314 depicting predictions of the progression of the patient's disease. Chart 312 depicts the probability of the patient either (i) recovering from the disease, (ii) living with the disease, or (iii) dying over a twenty-five year period. Chart 314 predicts the probability of the patient requiring assistive devices such as a feeding tube, a wheelchair, or a ventilator over the next twenty-five years.

The user interface can include a graphical element (not shown) that depicts the reliability of the prediction. For example, the graphical element can be modelled after traffic light. A red light can indicate that the prediction lacks a certain level of statistical significance. A yellow light can indicate that the prediction has an intermediate level of statistical significance. A green light can indicate that the prediction has an acceptable level of statistical significance.

The invention can also compute the effect of various stochastic and probabilistic events. For example, the invention can display two different predictions. The first prediction displays the progression of the patient's disease if the patient develops pneumonia; the second prediction displays the progression of the patient's disease if the patient does not develop pneumonia. The invention can also display advice on preventing pneumonia.

The invention can also incorporate the probability of such events into the predictive model. This can be accomplished, e.g., through the use of swarm or multiple agent simulation based on known state transition probabilities, as expressed in Markov chains. Sample measurements can then be taken at arbitrary points in time to determine probabilities of outcomes based on certain criteria. Such criteria can be controllable (e.g., receiving a certain intervention) or uncontrollable (e.g., developing pneumonia).

Additionally, the invention can simulate the effect of earlier actions that were either taken or not taken. For example, a patient can display the predicted disease progression for colon cancer if the cancer was detected two years earlier. Such a simulation can have a powerful effect on the patient's friends and family.

Verification of Predictions

In order to further refine the predictions, the methods described herein can include ways of verifying the accuracy of prior predictions. For example, if the algorithm predicts that a patient will be confined to a wheel chair by Feb. 1, 2009, the algorithm can send an email to the patient on or about this date to determine whether this prediction was accurate. Additionally or alternatively, the patient can continue to provide updated data to the algorithm that minimizes the need for follow up emails.

This newly acquired data is added to the population data and is reflected in further revisions of the predictive models.

Detection of Disease Subgroups

The invention also enables the detection of rare disease subgroups. For example, certain genotypes exhibit increased or decreased resistance to various diseases. Additional genotypes can be identified by detecting a group of patients that deviate substantially from the predicted disease progression and analyzing the genotypes and other data related to the patients.

Identification of New Interventions and Off-Label Uses of Medications

The invention also enables the identification of new interventions and off-label uses of medications. Such interventions and off-label uses can be effected by analyzing data for a population having a disease, identifying patients who experience an improvements in disease progression or symptom severity as a result of an intervention, and identifying the intervention. Given the potentially large size of patient communities, the invention is of particular value to pharmaceutical researchers looking to identify off-label uses of existing medications.

Software/Hardware Implementations

A web-based data-processing system can be used to implement the invention described herein. Web-based data-processing systems are well known in the art and can include a client computer and a server computer. The client and server computers can be coupled to each other over the Internet. Alternatively, the client and server computers can be coupled to each other over an intranet, for example, behind a firewall of a private corporate network. The private corporate network can be the network for a private hospital.

The client computer can include a client software program for executing software applications. The client software program can be an Internet browser such as INTERNET EXPLORER®, available from Microsoft Corporation of Redmond, Wash., FIREFOX®, available from the Mozilla Foundation of Mountain View, Calif., or OPERA®, available from Opera Software AS of Oslo, Norway. The Internet browser can display content encoded in a variety of standards such as Hyper Text Markup Language (HTML), and FLASH®, AIR®, and ACROBAT® platforms available from Adobe Systems of San Jose, Calif. User interfaces can include standard web input elements such as text boxes and toggle buttons for entering text and selecting options. The client computer can include input devices, such as a mouse, keyboard, or touch screen for entering information into the user interface.

The client computer need not be a personal computer per se, but rather encompasses devices such as handheld devices, personal digital assistants, and cellular phones. Mobile devices advantageously allow for more frequent data collection as well as well as reminders for patients to engage in an interventions such as consumption of medication. Suitable mobile device can be specifically constructed for the methods described herein or can be existing mobile devices such a smart phones available under the BLACKBERRY® trademark from Research in Motion Limited of Waterloo, Ontario, the PALM® trademark from Palm, Inc. of Sunnyvale, Calif., and the IPHONE™ trademark from Apple, Inc. of Cupertino, Calif.

The user interface can also be a text-based interface. For example, the server can send a text message or an email to a cellular phone or a smart phone asking how the patient is feeling. The patient can respond with an appropriate answer.

Likewise, the user interface can be an audio interface in which the server periodically places a telephone call to the patient asking how the patient is feeling. The patient can respond verbally, which will be then processed according to known voice recognition software.

The server computer can include a server software program including a web server, for example, Apache Server, and an application server, for example, Cold Fusion Application Server. The server computer can include a database server or engine for encoding and storing data. Suitable database software includes include DB2® and INFORMIX®, both available from IBM Corp. of Armonk, N.Y.; MICROSOFT JET® and MICROSOFT SQL SERVER®, both available from the Microsoft Corp. of Redmond, Wash.; MYSQL®, available from the MySQL Ltd. Co. of Stockholm, Sweden; ORACLE® Database, available from Oracle Int'l Corp of Redwood City, Calif.; and SYBASE®, available from Sybase, Inc. of Dublin, Calif.

The client software program can be used to provide a user interface for entering personalized data related to a patient, for example, a patient diagnosed with ALS. The personalized data can include patient name, sex, and age. The personalized data can include a medical condition metric, for example, whether a patient is feeling great, good, fair, poor, or awful. The personalized data can be submitted to the server software program and the server software program can receive the personalized data.

The server program can store the personalized data in memory on the server computer. The memory can be used to store a data structure including entries for the personalized data. The data structure can be a structured data file or a relational database.

The server software program can analyze the data, for example, using function calls executing on a microprocessor. The server software program can generate a graphical element for representing the personalized data and send the graphical element to the client software program. The graphical element can be sent over the Internet 162 and received by the client software program. The client software program can display the graphical element.

The graphical element can be generated and sent as an image or as a series of values for constructing the graphical element. The image can be sent to the client software program, which can display the image. Alternatively, a series of values can be sent to the client software program, which the client software program can use to construct and display the graphical element. For example, a plug-in executing in an Internet browser can be used to construct and display the graphical element. The plug-in can include special controls for interacting with the graphical element, including sliders for moving medical condition metrics.

The server software program can also store, analyze, generate, and send to the client software program medical outcome correlations for relating aspects of the medical condition, as further explained herein.

Administrative Tools

The invention includes an administrative tool for use by the scientific and medical staff to evaluate the models used to assess the progression and/or severity of disease. Using statistical techniques, the utility of every predictor variable in the database can be assessed by ranking the predictors by their $R^2$ values.

EXAMPLES

Example 1

Wheelchairs in ALS

A 55-year old male diagnosed with an inherited form of amyotrophic lateral sclerosis enters data stating that he has been tested for a mutation of the super-oxide-dismutase-1 gene (SODs) known as A4V (Alanine for Valine substitution at point 4). He enters data about his disease progression to-date using a self-report functional outcome scale on his profile in the online community.

An algorithm compares the likelihood of the patient reaching a given clinical milestone (e.g. needing a wheelchair, needing a ventilator, needing to use assistive technology to communicate) by creating a model comparing him to other patients with ALS that are similar in background and also have an A4V mutation.

The algorithm can be based on the ALSFRS. Typical rates of progression are linear with most patients progressing at a rate of 1 point per month. However, analysis of the dataset suggest patients with an A4V SODS mutation progress at a rate of 3 points per month.

The patient is presented with the option to see when certain health outcomes are likely to occur. If he decides to see the predicted results, he is shown a description of the system we have used to estimate the outcome. He then clicks on "proceed" and is shown his current progression plot with an overlaid curve progressing from the most recent datapoint/present time, to the predicted health outcomes. Rather than a simple line, the curve presents bands of varying widths according to (i) the quantity and quality of data provided by the individual and (i) the quantity and quality of data provided by other individuals like him in the system.

As the time of the predicted outcome approaches, the user is sent a private message asking him to validate the accuracy of the prediction made with regards to his health outcome, e.g., "In the past, you used our predictive outcome system to help you understand when you might need a wheelchair. At the time, our model of your disease progress suggested your disease state (as measured by your ALSFRS) would be 22 and you might need a wheelchair around 5 months from now. Please answer the FRS questionnaire. And, do you now use a wheelchair? If so please click "yes" and let us know from what date you started using a wheelchair. If not, please click "no". We will ask you again in 3 months' time."

Positive feedback gained from members decreases the confidence intervals surrounding predictions for a similar group of patients, i.e. in this example, future 55-year old male ALS patients with a SOD1 A4V mutation will see a narrower confidence interval around the predicted datapoint of needing a wheelchair. Negative feedback will lead to an increased confidence interval.

Members of scientific staff can evaluate the quality and confidence inherent in a particular model through use of a system tool viewable only by administrators of the website. Models with consistently poor feedback can be examined in detail and altered manually to improve performance.

Example 2

Excessive Gambling in Parkinson's Disease

A 75-year old male diagnosed with Parkinson's disease enters data stating that he has recently been prescribed the drug MIRAPEX® (pramipexol) at a rate of 2 mg per day. He enters data about his treatment regimen using a data-entry module which records his drug regime on his profile in the online community. He enters data that he has had a previous history of alcohol abuse, depression, and gambling.

An algorithm compares the likelihood of the patient reaching a given clinical milestone (e.g., developing a known side effect from the drug (pathological gambling), developing tolerance to the drug and needing a higher dose, finding an improvement in his physical health) by creating a model comparing him to other patients with Parkinson's disease that are similar in background and are also taking the same drug at a similar dosage.

The patient and other patients in the population enter data about at least two medical condition metrics. First, the patients self-report the severity of their Parkinson's Diseases by using a scale such as the Unified Parkinson's Disease Rating Scale (UPDRS). Second, the patient enter metrics to track problem gambling, the known side effect of pramipexol. Various scales exist to quantify problem gambling including the South Oaks Gambling Screen (SOGS), the Diagnostic and Statistical Manual of Mental Disorders (DSM-IV), and the Canadian Problem Gambling Severity Index (PGSI).

The patient is presented with the option to see whether certain health outcomes are likely to occur. If he decides to see the predicted results he is shown a description of the system we have used to come to estimate the outcome. He then clicks on "proceed" and is shown the current likelihood of experiencing side effects from the drug on the basis of known data from the clinical literature and/or from other members of the site. Rather than a simple number or percentage chance, the patient is presented with a spectrum of likelihood of varying widths according to (i) the quantity and quality of data provided by the individual and (ii) the quantity and quality of data provided by other individuals like him in the system.

As the time of the predicted outcome approaches, the user is sent a private message asking him to validate the accuracy of the prediction made with regards to his health outcome, e.g., "In the past, you used our predictive outcome system to help you understand whether you might experience a known side effect of MIRAPEX®, excessive gambling. At the time, our model of your disease progress suggested you had around a 20-40% chance of developing excessive gambling in the next 12 months. Have you found this to be true? If so please click "yes" and let us know from what date you started gambling excessively. If not, please click "no". We will ask you again in 3 months' time."

Positive feedback gained from members decreases the confidence intervals surrounding predictions for a similar group of patients, i.e. in this example, future 75-year old male Parkinson's disease patients with a history of alcoholism, depression, and gambling will see a narrower confidence interval around the predicted datapoint of developing a gambling problem. Negative feedback will lead to an increased confidence interval.

Members of scientific staff can evaluate the quality and confidence inherent in a particular model through use of a system tool viewable only by administrators of the website. Models with consistently poor feedback can be examined in detail and altered manually to improve performance.

Example 3

Rate of Progression in Huntington's Disease

A 38-year old male with a clinical diagnosis of Huntington's disease enters data stating that genetic testing by his clinician reveals that he has a relatively low number of pathological CAG repeats on the Huntington gene, having only 40 triple repeats. He enters data that he has a high level of education, a high socio-economic status, and a large family able to support him.

An algorithm evaluates the likelihood of him having to be looked after in a nursing home by creating a model comparing him to other patients with Huntington's disease that have a similar number of CAG repeats and also have a high level of education, a high socio-economic status, and a large family able to support him.

The algorithm can use self-reported of functionally ability from other population members as assessed by the Huntington's Disease Rating Scale (HDRS) to predict the patient's future functional ability.

The patient is presented with the option to see when certain health outcomes are likely to occur. If he decides to see the predicted results, he is shown a description of the system we have used to come to estimate the outcome. He then clicks on "proceed" and is shown the current likelihood of having to be cared for in a nursing home on the basis of known data from the clinical literature and/or from other members of the site. Rather than a simple number or percentage chance, the patient is presented with a spectrum of likelihood of varying widths according to (i) the quantity and quality of data provided by the individual and (ii) the quantity and quality of data provided by other individuals like him in the system.

As the time of the predicted outcome approaches, the user is sent a private message asking him to validate the accuracy of the prediction made with regards to his health outcome, i.e. "In the past, you used our predictive outcome system to help you understand whether you might need to be looked after in a care home. At the time, our model of your disease progress and family support suggested you had around a 2% chance of needing to be in a care home in the next 12 months. Have you found this to be true? If you did need to be in a care home please click "no" and let us know from what date you started being looked after in a care home. If not, please click "yes". We will ask you again in 12 months' time."

Positive feedback gained from members decreases the confidence intervals surrounding predictions for a similar group of patients, i.e. in this example, future 38-year old male Huntington's disease patients a high level of education, a high socio-economic status, and a large family able to support them will see a narrower confidence interval around the predicted datapoint of needing to be looked after in a care home. Negative feedback will lead to an increased confidence interval.

Members of scientific staff can evaluate the quality and confidence inherent in a particular model through use of a system tool viewable only by administrators of the website. Models with consistently poor feedback can be examined in detail and altered manually to improve performance.

Application to Depression

Some modern theories of depression posit that depression results from cognitive distortions. While all individuals become sad or upset at some points in time, most individuals have the perspective to recognize that such feeling are short-lived. However, individuals with a major depressive disorder are thought by some to lack the ability to recognize recall a time before they entered a depressive episode, and therefore cannot anticipate better times in the future.

The invention described herein are capable of helping persons dealing with depression. Depressed persons can enter their mood or other medical condition metrics into the systems described herein and retrieve graphical representations of these metrics over time. Such a system provides external memory and perspective for the patient.

Furthermore, the inventions described herein can be used by generally healthy individuals in advance of disease. For example, military personnel can record medical condition metrics before deployment to an armed conflict. Such prior medical condition metrics can serve both as a reference point for the military personnel when coping with conditions such a post traumatic stress disorder (PTSD) and to military health personnel seeking to screen for PTSD.

The functions of several elements can, in alternative embodiments, be carried out by fewer elements, or a single element. Similarly, any functional element can perform fewer, or different, operations than those described with respect to the illustrated embodiment. Also, functional elements (e.g., modules, databases, computers, clients, servers, and the like) shown as distinct for purposes of illustration can be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

Incorporation by Reference

All patents, published patent applications, and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Specifically, although this application periodically discusses the application of the invention to "diseases", the invention is equally applicable to other medical events such as aging, fertility, and the like. Such equivalents are intended to be encompassed by the following claims.

The invention claimed is:

1. A computer implemented method for providing real-time personalized medical predictions for an individual patient within a community of patients having a disease, the method comprising:
providing a plurality of computers each having a graphical user interface, each said computer being associated with a particular patient and including a processor configured with executable instructions to allow each patient of the community of patients to input self-reported information relating to one or more attributes of the particular patient without being responsive to a series of pre-programmed questions, the processor of each computer being further configured to;
receive self-reported patient information from a plurality of patients within the community of patients via the graphical user interface, the self-reported patient information including one or more attributes for each patient in the plurality of patients;
store the self-reported patient information in a database containing self-reported patient information for the community of patients;
construct a model of a disease based on disease progressions wherein a disease progression is based on a patient's disease and self-reported patient information stored in the database for a subset of the plurality of patients within the community of patients;
receive a request from an individual patient from the community of patients; and
determine a real-time prediction concerning the effect of an intervention for the individual patient based on the model and individual patient's attributes and analyzing an effect of the intervention by obtaining a difference between or comparing the outcome of a disease progress with and without an intervention.

2. The method of claim 1, wherein the one or more attributes includes at least one selected from the group consisting of: age, race, ethnicity, gender, height, weight, body mass index (BMI), body volume index (BVI), genotype, phenotype, severity of the disease, progression rate of the disease, measures of functional ability, quality of life, interventions, and remedies.

3. The method of claim 1, wherein the disease includes at least one selected from the group consisting of: neurological diseases, Amytrophric Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer, blood cancer, fibromyalgia, epilepsy, post traumatic stress disorder, traumatic brain injury, cardiovascular disease, osteoporosis, chronic obstructive pulmonary disease, arthritis, allergies, autoimmune diseases, and lupus.

4. The method of claim 1, wherein the model is based on data for a subset of the plurality of patients, and the method further comprises:
processing a request from the patient to modify a composition of the subset of the plurality of patients.

5. The method of claim 4, wherein the composition of the subset of other patients is defined by fuzzy logic.

6. The method of claim 4, wherein modifying the composition of the subset of the plurality of patients includes modifying the range of attributes of patients within the subset.

7. The method of claim 4, wherein modifying the composition of the subset of the plurality of the patients includes modifying the importance of attributes of patients in composing the subset.

8. The method of claim 1, further comprising:
conducting a multivariate pattern matching search of data related to the plurality of patients.

9. The method of claim 1, further comprising: calculating a confidence interval for the prediction.

10. The method of claim 9, wherein the confidence interval is calculated with a chi-square test.

11. The method of claim 9, wherein the confidence interval is calculated from a measure of variance of the individual patient's attributes.

12. The method of claim 9, wherein the confidence interval is calculated by comparing the individual patient's attributes to a model fit for the individual patient using the model.

13. The method of claim 9, wherein calculating a confidence interval for the prediction constitutes:
selecting a set of reported data points from the plurality of other patients;
for each of the reported data points in the set:
obtaining a data set for the corresponding other patient to the reported data point;
calculating a predicted value with the data set and the model; and
calculating an error between the predicted value and the reported data point;
producing a distribution of the errors; and
calculating a confidence interval from the distribution.

14. The method of claim 13, wherein the set of reported data points includes n closest reported data points to the prediction.

15. The method of claim 13, wherein the set of reported data points includes reported data points within an ellipsoid defined by a distance metric.

16. The method of claim 13, wherein a size of the data set for the corresponding other patient is comparable to a quantity of attributes associated with the individual patient.

17. The method of claim 1, wherein the difference is measured for a plurality of individual patients.

18. The method of claim 17, further comprising:
assembling a distribution of the differences for the plurality of individual patients; and
computing a standard error for the distribution.

19. The method of claim 1, wherein the difference is compared to the distribution error.

20. The method of claim 1, wherein the difference is compared to the confidence interval for the model.

21. The method of claim 20, further comprising:
identifying one or more of the differences that exceed the confidence interval for the model.

* * * * *